US012354256B2

(12) United States Patent
Besson et al.

(10) Patent No.: US 12,354,256 B2
(45) Date of Patent: Jul. 8, 2025

(54) BRAIN FEATURE PREDICTION USING GEOMETRIC DEEP LEARNING ON GRAPH REPRESENTATIONS OF MEDICAL IMAGE DATA

(71) Applicant: Northwestern University, Evanston, IL (US)

(72) Inventors: Pierre Alain Besson, Evanston, IL (US); Sarah Kathleen Bandt, Evanston, IL (US)

(73) Assignee: Northwestern University, Evanston, IL (US)

(*) Notice: Subject to any disclaimer, the term of this patent is extended or adjusted under 35 U.S.C. 154(b) by 922 days.

(21) Appl. No.: 17/505,465

(22) Filed: Oct. 19, 2021

(65) Prior Publication Data

US 2022/0122250 A1 Apr. 21, 2022

Related U.S. Application Data

(60) Provisional application No. 63/093,544, filed on Oct. 19, 2020.

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/4088* (2013.01); *A61B 5/4842* (2013.01);
(Continued)

(58) Field of Classification Search
CPC ......... G06T 7/0012; G06T 2207/10088; G06T 2207/20072; G06T 2207/20081;
(Continued)

(56) References Cited

U.S. PATENT DOCUMENTS

| 11,264,137 B1* | 3/2022 | Sughrue | ................ G16H 70/60 |
| 2010/0174171 A1* | 7/2010 | Lee | .......................... A61B 5/16 |
| | | | 600/410 |

(Continued)

OTHER PUBLICATIONS

Gopinath et al., "Learnable Pooling in Graph Convolution Networks for Brain Surface Analysis", arXiv:1911.10129v1 [cs.CV] Nov. 22, 2019, pp. 1-10 (Year: 2019).*

(Continued)

*Primary Examiner* — Ping Y Hsieh
*Assistant Examiner* — Jose M Torres
(74) *Attorney, Agent, or Firm* — Quarles & Brady LLP

(57) ABSTRACT

Described here are systems and method for predicting clinically relevant brain features using geometric deep learning techniques, such as may be implemented with graph convolutional neural networks or autoencoder networks that are applied to graph representations of brain surface morphology derived from medical images. As an example, graph convolutional neural networks can be applied to brain surface morphology data derived from magnetic resonance images (e.g., T1-weighted) using surface extraction techniques in order to predict brain feature data.

22 Claims, 21 Drawing Sheets
(15 of 21 Drawing Sheet(s) Filed in Color)

(51) Int. Cl.
*G06N 3/08* (2023.01)
*G16H 15/00* (2018.01)
*G16H 30/40* (2018.01)
*G16H 50/20* (2018.01)
*G16H 50/30* (2018.01)

(52) U.S. Cl.
CPC ............. *A61B 5/4848* (2013.01); *G06N 3/08* (2013.01); *G16H 30/40* (2018.01); *G16H 50/20* (2018.01); *G16H 50/30* (2018.01); *G06T 2207/20081* (2013.01); *G06T 2207/20084* (2013.01); *G06T 2207/30016* (2013.01); *G16H 15/00* (2018.01)

(58) Field of Classification Search
CPC . G06T 2207/20084; G06T 2207/30016; A61B 5/4088; A61B 5/4842; A61B 5/4848; G06N 3/045; G06N 3/047; G06N 3/048; G06N 3/08; G16H 15/00; G16H 30/20; G16H 30/40; G16H 40/67; G16H 50/20; G16H 50/30; G16H 50/70
See application file for complete search history.

(56) References Cited

U.S. PATENT DOCUMENTS

| | | | | |
|---|---|---|---|---|
| 2016/0306023 | A1* | 10/2016 | Zagorchev | G01R 33/4828 |
| 2018/0268942 | A1* | 9/2018 | Kamali-Zare | G06T 17/10 |
| 2019/0102511 | A1* | 4/2019 | Murray | G16B 40/00 |
| 2019/0148021 | A1* | 5/2019 | Styner | G06N 20/10 705/2 |
| 2020/0311926 | A1* | 10/2020 | Tian | G06T 3/4053 |
| 2020/0357119 | A1* | 11/2020 | Siemionow | G16H 30/40 |
| 2022/0051801 | A1* | 2/2022 | Feng | G06T 7/0012 |
| 2022/0130065 | A1* | 4/2022 | Hong | G06T 7/62 |
| 2022/0284578 | A1* | 9/2022 | Patil | G06T 7/0012 |

OTHER PUBLICATIONS

Awate, S. P., P. Yushkevich, D. Licht and J. C. Gee (2009). "Gender differences in cerebral cortical folding: multivariate complexity-shape analysis with insights into handling brain-volume differences." Med Image Comput Comput Assist Interv 12(Pt 2):200-207.

Awate, S. P., P. A. Yushkevich, Z. Song, D. J. Licht and J. C. Gee (2010). "Cerebral cortical folding analysis with multivariate modeling and testing: Studies on gender differences and neonatal development." Neuroimage 53(2):450-459.

Bernal, J., K. Kushibar, D. S. Asfaw, S. Valverde, A. Oliver, R. Marti and X. Lladó (2019). "Deep convolutional neural networks for brain image analysis on magnetic resonance imaging: a review." Artificial Intelligence in Medicine 95:64-81.

Besson, P., F. Andermann, F. Dubeau and A. Bernasconi (2008). "Small focal cortical dysplasia lesions are located at the bottom of a deep sulcus." Brain 131(12): 3246-3255.

Bronstein MM, B. J., LeCun Y, Szlam A, & Vandergheynst P (2017). "Geometric Deep Learning: Going beyond Euclidean data." Ieee Signal Proc Mag 34(4): 18-42.

Cachia, A., M.-L. Paillere-Martinot, A. Galinowski, D. Januel, R. de Beaurepaire, F. Bellivier, E. Artiges, J. Andoh, D. Bartrés-Faz, E. Duchesnay, D. Rivière, M. Plaze, J.-F. Mangin and J.-L. Martinot (2008). "Cortical folding abnormalities In schizophrenia patients with resistant auditory hallucinations." Neuroimage 39(3): 927-935.

Cachia, A., M. Roell, J.-F. Mangin, Z. Y. Sun, A. Jobert, L. Braga, O. Houde, S. Dehaene and G. Borst (2018). "How Interindividual differences in brain anatomy shape reading accuracy." Brain Structure and Function 223(2): 701-712.

Caviness, V. S. (1975). "Mechanical model of brain convolutional development." Science 189(4196): 18.

Creze, M., L. Versheure, P. Besson, C. Sauvage, X. Leclerc and P. Jissendi-Tchofo (2014). "Age- and gender-related regional variations of human brain cortical thickness, complexity, and gradient in the third decade." Hum Brain Mapp 35(6): 2817-2835.

Dale, A. M., B. Fischl and M. I. Sereno (1999). "Cortical Surface-Based Analysis: I. Segmentation and Surface Reconstruction." NeuroImage 9(2): 179-194.

Defferrard, M., X. Bresson and P. Vandergheynst (2016). Convolutional neural networks on graphs with fast localized spectral filtering. Advances in Neural Information Processing Systems.

Dubois, J., M. Benders, C. Borradori-Tolsa, A. Cachia, F. Lazeyras, R. Ha-Vinh Leuchter, S. V. Sizonenko, S. K. Warfield, J. F. Mangin and P. S. Huppi (2008). "Primary cortical folding in the human newborn: an early marker of later functional development." Brain 131(8): 2028-2041.

Fischl, B., N. Rajendran, E. Busa, J. Augustinack, O. Hinds, B. T. T. Yeo, H. Mohlberg, K. Amunts and K. Zilles (2008). "Cortical Folding Patterns and Predicting Cytoarchitecture." Cerebral Cortex 18(8): 1973-1980.

Fischl, B., M. I. Sereno and A. M. Dale (1999). "Cortical Surface-Based Analysis: II: Inflation, Flattening, and a Surface-Based Coordinate System." NeuroImage 9(2): 195-207.

Fischl, B., M. I. Sereno, R. B. Tootell and A. M. Dale (1999). "High-resolution intersubject averaging and a coordinate system for the cortical surface." Hum Brain Mapp 8(4): 272-284.

Franke, K., G. Ziegler, S. Kloppel and C. Gaser (2010). "Estimating the age of healthy subjects from T1-weighted MRI scans using kernel methods: Exploring the influence of various parameters." NeuroImage 50(3): 883-892.

Gogtay, N., J. N. Giedd, L. Lusk, K. M. Hayashi, D. Greenstein, A. C. Vaituzis, T. F. Nugent, D. H. Herman, L. S. Clasen, A. W. Toga, J. L. Rapoport and P. M. Thompson (2004). "Dynamic mapping of human cortical development during childhood through early adulthood." Proc Natl Acad Sci U S A 101(21): 8174-8179.

Gutierrez Becker, B., T. Klein and C. Wachinger (2018). "Gaussian process uncertainty in age estimation as a measure of brain abnormality." NeuroImage 175: 246-258.

Hammond, D. K., P. Vandergheynst and R. Gribonval (2011). "Wavelets on graphs via spectral graph theory." Applied and Computational Harmonic Analysis 30(2): 129-150.

He, K. M., X. Y. Zhang, S. Q. Ren and J. Sun (2016). "Deep Residual Learning for Image Recognition." 2016 Ieee Conference on Computer Vision and Pattern Recognition (Cvpr): 770-778.

Hilgetag, C. and H. Barbas (2005). "Developmental mechanics of the primate cerebral cortex." Anatomy and Embryology 210(5-6): 411-417.

Im, K., J.-M. Lee, U. Yoon, Y.-W. Shin, S. B. Hong, I. Y. Kim, J. S. Kwon and S. I. Kim (2006). "Fractal dimension in human cortical surface: Multiple regression analysis with cortical thickness, sulcal depth, and folding area." Human Brain Mapping 27(12): 994-1003.

Im, K., J. M. Lee, J. Lee, Y. W. Shin, I. Y. Kim, J. S. Kwon and S. I. Kim (2006). "Gender difference analysis of cortical thickness in healthy young adults with surface-based methods." Neuroimage 31(1): 31-38.

Jimenez, L. O. and D. A. Landgrebe (1998). "Supervised classification in high-dimensional space: geometrical, statistical, and asymptotical properties of multivariate data." IEEE Transactions on Systems, Man, and Cybernetics, Part C (Applications and Reviews) 28(1): 39-54.

Jockwitz, C., S. Caspers, S. Lux, K. Jutten, A. Schleicher, S. B. Eickhoff, K. Amunts and K. Zilles (2017). "Age- and function-related regional changes in cortical folding of the default mode network in older adults." Brain Struct Funct 222(1): 83-99.

Kingma, D. P. and J. J. a. p. a. Ba (2014). "Adam: A method for stochastic optimization."

Kochunov, P., J.-F. Mangin, T. Coyle, J. Lancaster, P. Thompson, D. Rivière, Y. Cointepas, J. Regis, A. Schlosser, D. R. Royall, K. Zilles, J. Mazziotta, A. Toga and P. T. Fox (2005). "Age-related morphology trends of cortical sulci." Human Brain Mapping 26(3): 210-220.

Kroenke, C. D. and P. V. Bayly (2018). "How Forces Fold the Cerebral Cortex." The Journal of Neuroscience 38(4): 767.

LeCun, Y., Y. Bengio and G. Hinton (2015). "Deep learning." Nature 521: 436.

Lemaitre, H., A. L. Goldman, F. Sambataro, B. A. Verchinski, A. Meyer-Lindenberg, D. R. Weinberger and V. S. Mattay (2012).

(56) References Cited

OTHER PUBLICATIONS

"Normal age-related brain morphometric changes: nonuniformity across cortical thickness, surface area and gray matter volume?" Neurobiol Aging 33(3): 617.e611-619.

Lemaître, H., F. Crivello, B. Grassiot, A. Alperovitch, C. Tzourio and B. Mazoyer (2005). "Age- and sex-related effects on the neuroanatomy of healthy elderly." Neuroimage 26(3): 900-911.

Liu, T., W. Wen, W. Zhu, J. Trollor, S. Reppermund, J. Crawford, J. S. Jin, S. Luo, H. Brodaty and P. Sachdev (2010). "The effects of age and sex on cortical sulci in the elderly." Neuroimage 51(1): 19-27.

Luders, E., K. L. Narr, R. M. Bilder, P. R. Szeszko, M. N. Gurbani, L. Hamilton, A. W. Toga and C. Gaser (2008). "Mapping the relationship between cortical convolution and intelligence: effects of gender." Cereb Cortex 18(9): 2019-2026.

Luders, E., P. M. Thompson, K. L. Narr, A. W. Toga, L. Jancke and C. Gaser (2006). "A curvature-based approach to estimate local gyrification on the cortical surface." Neuroimage 29(4): 1224-1230.

Luders, E. and A. W. Toga (2010). "Sex differences in brain anatomy." Prog Brain Res 186: 3-12.

Lv, B., J. Li, H. He, M. Li, M. Zhao, L. Ai, F. Yan, J. Xian and Z. Wang (2010). "Gender consistency and difference in healthy adults revealed by cortical thickness." Neuroimage 53(2): 373-382.

Madan, C. R. and E. A. Kensinger (2016). "Cortical complexity as a measure of age-related brain atrophy." Neuroimage 134: 617-629.

McGinnis, S. M., M. Brickhouse, B. Pascual and B. C. Dickerson (2011). "Age-related changes in the thickness of cortical zones in humans." Brain Topogr 24(3-4): 279-291.

Nieuwenhuis, M., H. G. Schnack, N. E. van Haren, J. Lappin, C. Morgan, A. A. Reinders, D. Gutierrez-Tordesillas, R. Roiz-Santianez, M. S. Schaufelberger, P. G. Rosa, M. V. Zanetti, G. F. Busatto, B. Crespo-Facorro, P. D. McGorry, D. Velakoulis, C. Pantelis, S. J. Wood, R. S. Kahn, J. Mourao-Miranda and P. Dazzan (2017). "Multi-center MRI prediction models: Predicting sex and illness course in first episode psychosis patients." NeuroImage 145: 246-253.

Nopoulos, P., M. Flaum, D. O'Leary and N. C. Andreasen (2000). "Sexual dimorphism in the human brain: evaluation of tissue volume tissue composition and surface anatomy using magnetic resonance imaging." Psychiatry Res 98(1): 1-13.

Nordahl, C. W., D. Dierker, I. Mostafavi, C. M. Schumann, S. M. Rivera, D. G. Amaral and D. C. Van Essen (2007). "Cortical Folding Abnormalities in Autism Revealed by Surface-Based Morphometry." The Journal of Neuroscience 27(43): 11725.

Penttilä, J., M.-L. Paillère-Martinot, J.-L. Martinot, D. Ringuenet, M. Wessa, J. Houenou, T. Gallarda, F. Bellivier, A. Galinowski, P. Bruguière, F. Pinabel, M. Leboyer, J.-P. Olié, E. Duchesnay, E. Artiges, J.-F. Mangin and A. Cachia (2009). "Cortical folding in patients with bipolar disorder or unipolar depression." Journal of psychiatry & neuroscience : JPN 34(2): 127-135.

Pinaya, W. H. L., A. Mechelli and J. R. Sato (2018). "Using deep autoencoders to identify abnormal brain structural patterns in neuropsychiatric disorders: A large-scale multi-sample study." Human Brain Mapping 0(0).

Rakic, P. (1988). "Specification of cerebral cortical areas." Science 241(4862): 170.

Salat, D. H., S. Y. Lee, A. J. van der Kouwe, D. N. Greve, B. Fischl and H. D. Rosas (2009). "Age-associated alterations in cortical gray and white matter signal intensity and gray to white matter contrast." Neuroimage 48(1): 21-28.

Schaer, M., M. B. Cuadra, L. Tamarit, F. Lazeyras, S. Eliez and J. Thiran (2008). "A Surface-Based Approach to Quantify Local Cortical Gyrification." IEEE Transactions on Medical Imaging 27(2): 161-170.

Schmitgen, M. M., M. S. Depping, C. Bach, N. D. Wolf, K. M. Kubera, N. Vasic, D. Hirjak, F. Sambataro and R. C. Wolf (2019). "Aberrant cortical neurodevelopment in major depressive disorder." Journal of Affective Disorders 243: 340-347.

Shaw, P., D. Greenstein, J. Lerch, L. Clasen, R. Lenroot, N. Gogtay, A. Evans, J. Rapoport and J. Giedd (2006). "Intellectual ability and cortical development in children and adolescents." Nature 440(7084): 676-679.

Sherif, T., P. Rioux, M.-E. Rousseau, N. Kassis, N. Beck, R. Adalat, S. Das, T. Glatard and A. C. Evans (2014). "CBRAIN: a web-based, distributed computing platform for collaborative neuroimaging research." 8(54).

Shuman, D. I., S. K. Narang, P. Frossard, A. Ortega and P. Vandergheynst (2013). "The Emerging Field of Signal Processing on Graphs." Ieee Signal Processing Magazine 30(3): 83-98.

Sowell, E. R., B. S. Peterson, E. Kan, R. P. Woods, J. Yoshii, R. Bansal, D. Xu, H. Zhu, P. M. Thompson and A. W. Toga (2007). "Sex differences in cortical thickness mapped in 176 healthy individuals between 7 and 87 years of age." Cereb Cortex 17(7): 1550-1560.

Thompson, P. M., A. D. Lee, R. A. Dutton, J. A. Geaga, K. M. Hayashi, M. A. Eckert, U. Bellugi, A. M. Galaburda, J. R. Korenberg, D. L. Mills, A. W. Toga and A. L. Reiss (2005). "Abnormal Cortical Complexity and Thickness Profiles Mapped in Williams Syndrome." The Journal of Neuroscience 25(16): 4146.

Toro, R., M. Perron, B. Pike, L. Richer, S. Veillette, Z. Pausova and T. Paus (2008). "Brain Size and Folding of the Human Cerebral Cortex." Cerebral Cortex 18(10): 2352-2357.

Valizadeh, S. A., J. Hänggi, S. Mérillat and L. Jancke (2016). "Age prediction on the basis of brain anatomical measures." Human Brain Mapping 38(2): 997-1008.

Van Essen, D. C. (1997). "A tension-based theory of morphogenesis and compact wiring in the central nervous system." Nature 385(6614): 313-318.

Wachinger, C., P. Golland, W. Kremen, B. Fischl and M. Reuter (2015). "BrainPrint: A discriminative characterization of brain morphology." NeuroImage 109: 232-248.

Wang, Z. and J. J. a. p. a. Yang (2017). "Diabetic Retinopathy Detection via Deep Convolutional Networks for Discriminative Localization and Visual Explanation."

Westlye, L. T., K. B. Walhovd, A. M. Dale, A. Bjørnerud, P. Due-Tønnessen, A. Engvig, H. Grydeland, C. K. Tamnes, Y. Østby and A. M. Fjell (2010). "Differentiating maturational and aging-related changes of the cerebral cortex by use of thickness and signal intensity." Neuroimage 52(1): 172-185.

Whittle, S., N. B. Allen, A. Fornito, D. I. Lubman, J. G. Simmons, C. Pantelis and M. Yücel (2009). "Variations in cortical folding patterns are related to individual differences in temperament." Psychiatry Research: Neuroimaging 172 (1): 68-74.

Zhou, B., A. Khosla, A. Lapedriza, A. Oliva and A. Torralba (2016). "Learning Deep Features for Discriminative Localization." 2016 Ieee Conference on Computer Vision and Pattern Recognition (Cvpr): 2921-2929.

Zilles, K. and K. Amunts (2010). "Centenary of Brodmann's map—conception and fate." Nature Reviews Neuroscience 11: 139.

Zilles, K., E. Armstrong, A. Schleicher and H. J. Kretschmann (1988). "The human pattern of gyrification in the cerebral cortex." Anat Embryol (Berl) 179(2): 173-179.

* cited by examiner

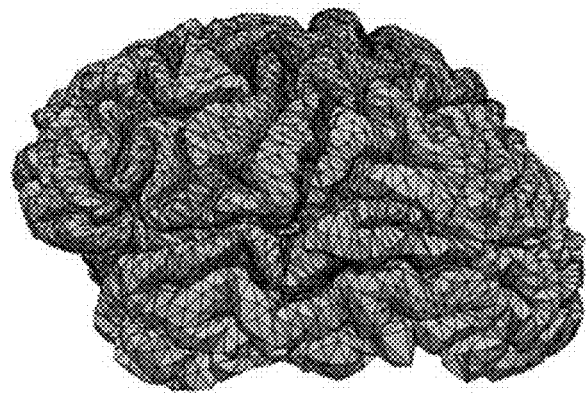
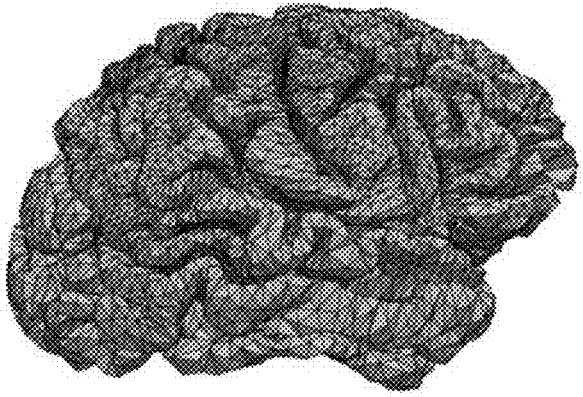
FIG. 8A               FIG. 8B
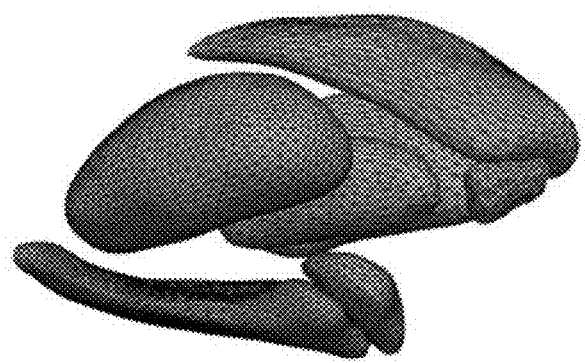
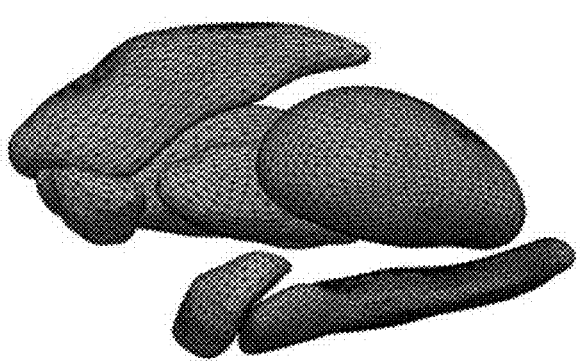
FIG. 8C               FIG. 8D

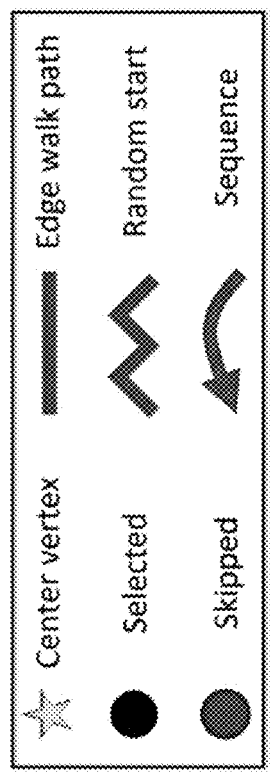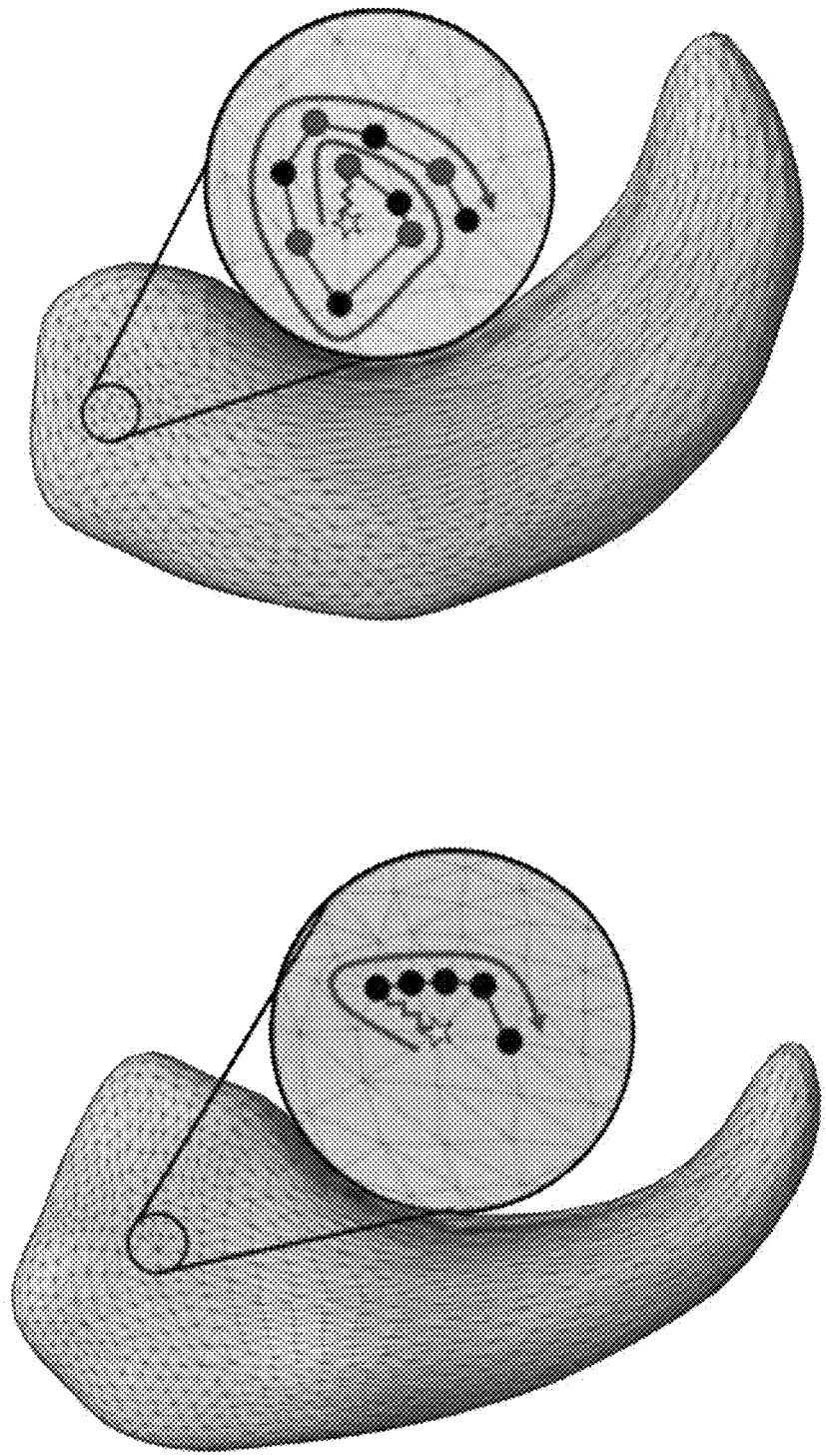
FIG. 12B
FIG. 12A ly the inner cortical surfaces, or the inner and outer cortical surfaces. The color indicates cortical areas with either low or high involvement in the decision.

BRAIN FEATURE PREDICTION USING GEOMETRIC DEEP LEARNING ON GRAPH REPRESENTATIONS OF MEDICAL IMAGE DATA

CROSS-REFERENCE TO RELATED APPLICATIONS

This application claims the benefit of U.S. Provisional Patent Application Ser. No. 63/093,544, filed on Oct. 19, 2020, and entitled "BRAIN FEATURE PREDICTION VIA GRAPH CONVOLUTIONAL NEURAL NETWORK ANALYSIS," which is herein incorporated by reference in its entirety.

STATEMENT REGARDING FEDERALLY SPONSORED RESEARCH

This invention was made with government support under AG067069 awarded by the National Institutes of Health. The government has certain rights in the invention.

BACKGROUND

Deep learning is a data-driven machine learning tool that can obviate the need for manual feature selection. One advantage of deep learning is its ability to learn the most relevant features of a dataset without any prior knowledge. Convolutional neural networks ("CNN") are one example of a deep learning architecture, and are particularly well-suited for a range of image processing tasks. CNNs rely on data being represented on regular Euclidean grids, which restricts the use of CNNs in many neuroimaging tasks. This property of CNNs also prevents their use on non-Euclidean datasets, such as surface meshes and connectivity graphs, which can each provide unique information about the brain. The ability to apply CNNs to a wider range of neuroimaging tasks is desirable.

SUMMARY OF THE DISCLOSURE

The present disclosure addresses the aforementioned drawbacks by providing a method for generating brain feature data from medical images. Medical image data are accessed with a computer system, where the medical image data include medical images that depict a brain of a subject. A neural network is also accessed with the computer system, where the neural network is trained to take input as brain surface data and generate output as brain feature data. Brain surface data are generated from the medical image data using the computer system, where the brain surface data represent at least one of a cortical surface or a subcortical surface of the subject's brain. Graph representation data of the brain surface data are generated using the computer system, where the graph representation data represent a brain surface as a graph of connected nodes. The graph representation data are input to the neural network, generating output as brain feature data that indicate at least one brain feature of the subject's brain. The brain feature data are then outputted to a user.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 8A-8D show example cortical and subcortical meshes. Presented are lateral views of a left hemisphere cortical mesh (FIG. 8A) and right hemisphere cortical mesh (FIG. 8B). Medial views of a left hemisphere subcortical mesh (FIG. 8C) and right hemisphere subcortical mesh (FIG. 8D) are also shown.

(FIGS. 11A, 11B, 11E, 11F) lateral-medial views of the left hemisphere respectively, (FIGS. 11C, 11D, 11G, 11H) medial-lateral views of the right hemisphere respectively.

FIGS. 12A and 12B illustrate examples of spiral sequences established on left hippocampi triangular meshes from randomly selected scans of a subject with Alzheimer's disease (FIG. 12A) and a healthy control (FIG. 12B). Note that in using dilation, the receptive field of the kernel supports exponential expansion without increasing the support size/length of the spiral kernel. In each example, a spiral sequence of 6 selected vertices are generated including the center vertex.

FIGS. 19A and 19B are visualizations training with all cortical and subcortical structures (All). FIGS. 19C and 19D are visualizations training with only cortical (Only-cortical) or subcortical structures (Only-subcortical).

FIGS. 20A and 20B are visualizations training with all cortical and subcortical structures (All). FIGS. 20C and 20D are visualizations training with only cortical (Only-cortical) or subcortical structures (Only-subcortical).

DETAILED DESCRIPTION

Figure 1:
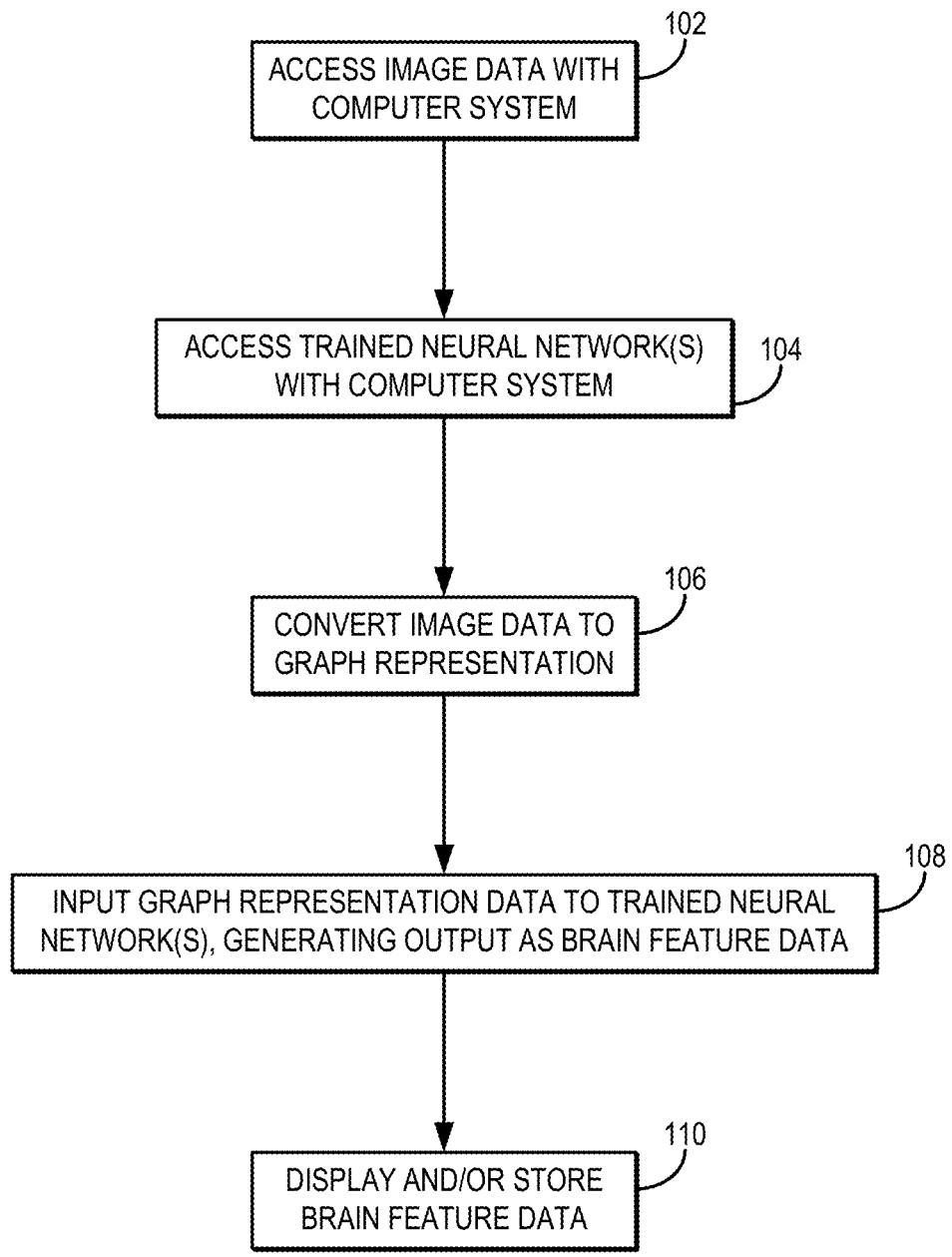
FIG. 1 is a flowchart setting forth the steps of an example method for generating brain feature data from image data, such as magnetic resonance images, using a trained neural network, such as a trained graph convolutional neural network or autoencoder network.

Described here are systems and method for predicting clinically relevant brain features, such as demographic information (e.g., age, sex) and/or disease state (e.g., Alzheimer's disease, epilepsy), using geometric deep learning techniques, such as may be implemented with graph convolutional neural networks or autoencoder networks that are applied to graph representations of brain surface morphology. As an example, graph convolutional neural networks can be applied to brain surface morphology data derived from magnetic resonance images (e.g., T1-weighted) using surface extraction techniques in order to predict brain feature data.

The disclosed systems and methods offer advantages over current methods. As one example, deep learning obviates feature selection. As a result, the systems and methods described in the present disclosure provide an unbiased neuroimaging tool. As another example, the multi-scale nature of the systems and methods described in the present disclosure facilitates the investigation of complex, network-based brain disorders, such as Alzheimer's disease (including other conditions along the AD spectrum including mild cognitive impairment (e.g., a "pre-AD" state)).

The systems and methods described in the present disclosure have applications in various clinical and biomedical applications. As one example, the systems and methods can be implemented as a biomedical research tool across a wide range of neurologic and psychiatric disorders (e.g., Alzheimer's disease, epilepsy, Parkinson's disease, multiple sclerosis, stroke, autism, ADHD, depression, anxiety, PTSD, brain metastases, brain tumor diagnosis and management, among many others). As another example, the systems and methods can be implemented to investigate or otherwise monitor relationships between remote brain regions in individuals.

Advantageously, the systems and methods described in the present disclosure can be used for clinical applications, such as epilepsy patient management, Parkinson's disease patient management, multiple sclerosis patient management, stroke risk and outcome prediction, TBI outcome prediction, among others.

As another example, the systems and methods can be used to generate brain feature data that may predict or otherwise quantify or qualify one or more features of a subject's brain. For instance, the systems and methods can be used to estimate a "brain age" score for a subject, which can be used for quantifying or otherwise estimating Alzheimer's disease risk prediction and/or risk factor modification. These brain age scores can be used for brain age prediction in addition to generating an Alzheimer's disease risk factor profile report, which may indicate a risk of developing Alzheimer's disease within a selected or otherwise identified duration of time, in addition to lifestyle modifications that could minimize that risk. Similarly, the systems and methods can be used to estimate brain feature data and/or scores that can be used to predict other neurological conditions, including stroke risk prediction.

More generally, the systems and methods described in the present disclosure can be used for a variety of applications throughout neuroscience and clinical medicine in order to predict and/or quantify features indicative of, associated with, or related to a range of neuroscientific, neurodevelopmental, and clinical brain related conditions including defining neurocognitive and/or neurobehavioral developmental trajectories, early diagnosis of a wide range of neurologic conditions, and characterizing the aging spectrum from infancy through death. As another non-limiting example, the output brain feature data can indicate or otherwise predict fluid intelligence in individuals across the aging spectrum. Additionally or alternatively, the output brain feature data can predict or otherwise quantify other cognitive and/or behavioral measures.

The systems and methods described in the present disclosure provide the following advantages: they are unbiased, data-driven, provide the ability to map relevant brain regions involved in prediction, can be used with commonly available T1-weighted MRI data, provide the ability to integrate with connectivity analysis (e.g., functional connectivity analysis), and have the potential to bring Alzheimer's and stroke risk prediction and risk-factor modification to the forefront of lay culture.

Referring now to FIG. 1, a flowchart is illustrated as setting forth the steps of an example method 100 for generating brain feature data using a suitably trained neural network or other machine learning algorithm.

The method includes accessing image data with a computer system, as indicated at step 102. As an example, the image data may include medical image data, such as images obtained with a magnetic resonance imaging ("MRI") system, a positron emission tomography ("PET") system, an x-ray computed tomography ("CT") system, or other suitable medical imaging system. Additionally or alternatively, other types of medical images or other image data may also be accessed. Accessing the image data may include retrieving such data from a memory or other suitable data storage device or medium. Alternatively, accessing the image data may include acquiring such data with an imaging system, such as an MRI system, and transferring or otherwise communicating the data to the computer system, which may be a part of the imaging system.

In general, the image data depict the brain of a subject. For example, the image data may be magnetic resonance image data including T1-weighted or other magnetic resonance images that depict the brain of a subject. The images can depict, for example, white matter, gray matter, and/or cerebrospinal fluid. As described below, using the image data various different brain surfaces can be extracted, including inner cortical surfaces, outer cortical surfaces, and/or subcortical surfaces. The extracted brain surfaces can be converted to a graph representation (e.g., by generating a triangular or other mesh of the surface and converting the mesh into a graph representation), as will be described below in more detail.

A trained neural network (or other suitable machine learning algorithm) is then accessed with the computer system, as indicated at step 104. As one example, the trained neural network may be a graph convolutional neural network. As another example, the trained neural network may be an autoencoder network, such as a surface-based deep autoencoder, a graph variational autoencoder, a conditional variational autoencoder, or the like. Accessing the trained neural network may include accessing network parameters (e.g., weights, biases, or both) that have been optimized or otherwise estimated by training the neural network on training data. In some instances, retrieving the neural network can also include retrieving, constructing, or otherwise accessing the particular neural network architecture to be implemented. For instance, data pertaining to the layers in the neural network architecture (e.g., number of layers, type of layers, ordering of layers, connections between layers, hyperparameters for layers) may be retrieved, selected, constructed, or otherwise accessed.

In general, the neural network is trained, or has been trained, on training data in order to estimate, predict, or otherwise quantify or qualify brain features from brain surfaces (e.g., cortical surfaces, subcortical surfaces) extracted from medical images, such as magnetic resonance images, which may be T1-weighted magnetic resonance images, T2-weighted images, diffusion-weighted images, combinations thereof, or the like.

The image data are then converted into a graph representation, generating output as graph representation data, as indicated at step 106. In general, the graph representation data can include vertices and edges, which can define nodes and edges of a graph. The graph provides the underlying structure of the data (e.g., the extracted brain surfaces), in particular the relationships between its nodes.

As one example, when the image data depict a subject's brain, converting the image data into a graph representation can include extracting or otherwise generating a brain surface (e.g., cortical surface, subcortical surface) from the image data, generating output as brain surface data. In such instances, the brain surface (e.g., cortical surface, subcortical surface) can be a triangulated mesh composed of a number of vertices per hemisphere connected to form triangles. The nodes of the graph can be defined as the vertices of the brain surface mesh and the edges can be defined as the links of the triangles. In some instances, the edges can be defined as the links of the triangles weighted as a function of the length of the link, such as $$W_{i,j} = \frac{e^{-\frac{\Delta_{i,j}^2}{2}}}{\sqrt{2\pi}}; \tag{1}$$

where $\Delta_{i,j}$ is the Euclidean distance between vertices i and j. A function, F, can be defined at the nodes of the graph, G, and can be used as the input to the train neural network. For instance, the function, F, can be the vertex coordinates registered to the MNI space, registered and resampled to a common surface space. In this example, each vertex can have six features if both the inner and outer cortical surfaces are used (x, y, and z coordinates of both white and pial surfaces), or three features if only the inner cortical surfaces are used (x, y, z coordinates of the white surface only).

Thus, converting the image data to the graph representation can include first extracting or otherwise generating one or more mesh surfaces from the image data and then converting the mesh surface(s) to a graph representation.

In some embodiments, converting the image data to the graph representation data can include generating a brain surface mesh, as described above, and determining one or more spiral sequences on the brain surface mesh, as described below in more detail.

As another example, the image data can also be directly converted into graph representation data. For example, the image signals (or characteristics thereof) in the image data can be mapped or otherwise converted onto a grid or other geometric framework that can be represented as a graph. Thus, the signals (or signal characteristics) in the image data can be directly converted into a graph representation, such that the nodes in the graph are representative of image signals having been mapped into geometric data.

The graph representation data are then input to the trained neural network(s), generating output as brain feature data, as indicated at step 108. For example, the brain feature data may include feature maps associated with one or more various brain features. The feature maps may depict the spatial distribution or spatial patterns of features, statistics, or other parameters associated with one or more brain features, including demographic information (e.g., age, sex) and disease state (e.g., Alzheimer's disease, epilepsy). Additionally or alternatively, the brain feature data may include scores that quantify one or more parameters associated with one or more brain features.

As one example, the feature maps may indicate the local probability for a particular classification (i.e., the probability that a voxel belongs to a particular class) or other prediction. For instance, the feature maps may indicate the location and/or probability of a brain region being associated with a particular brain feature (e.g., brain age score or disease state).

As another example, the feature maps may indicate a classification or other prediction of the input image data (e.g., by assigning a particular classification to each voxel in the feature map).

Additionally or alternatively, the brain feature data may include class activation maps (and/or regression activation maps), which are visually interpretable heatmaps that localize areas on the brain surface mesh(es) that drive true positive predictions of the classified brain feature or condition (e.g., age, sex, disease state).

In still other examples, the brain feature data may include one or more score values, such as a fluid intelligence score, Gf, value.

The brain feature data generated by inputting the graph representation data to the trained neural network(s) can then be displayed to a user, stored for later use or further processing, or both, as indicated at step 110.

In one example, the systems and methods described in the present disclosure can be implemented to predict or otherwise characterize a condition of a subject's brain, such as a prediction or probability of a subject's sex and/or age, or whether the subject has or will develop a disease (e.g., Alzheimer's disease) or another neurological condition. In this example, a graph convolutional network is implemented, as described below in more detail.

As described above with respect to step 102 of method 100, image data are accessed with a computer system. In this example, the image data include magnetic resonance image data, such as T1-weighted images. The image data can be preprocessed or otherwise prepared for conversion to a graph representation.

Figure 2:
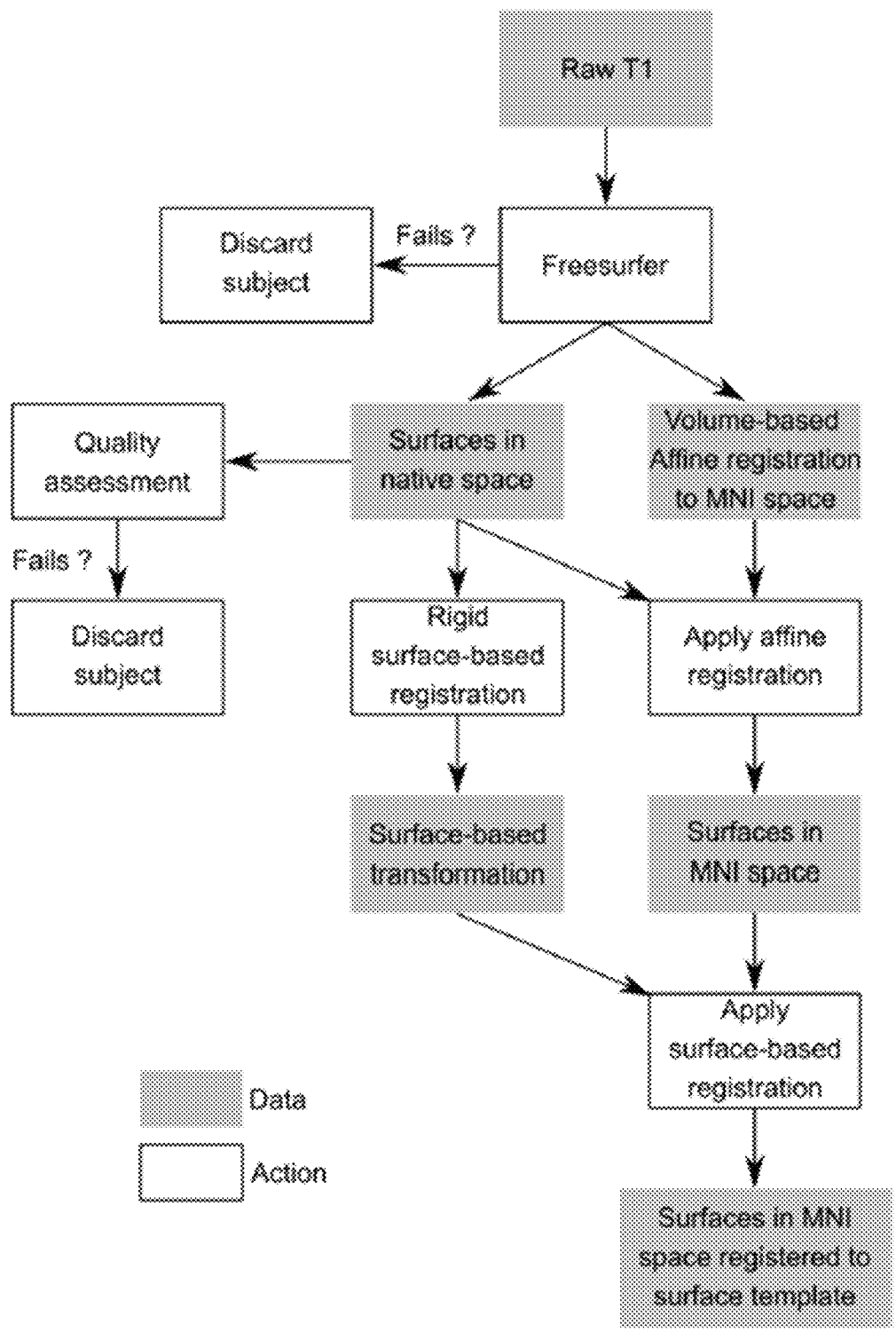
FIG. 2 is a flowchart of an example image data preparation process. After cortical surfaces are extracted (e.g., using Freesurfer), they are affinely registered to the MNI space and rigidly registered with the surface template to ensure vertex-wise correspondence. Quality assessment can be used to ensure that the quality of surface extraction and registration is satisfactory.

An example data preparation process that can be used to extract or otherwise generate brain surface data (e.g., brain surface meshes) from image data is illustrated in FIG. 2. The following preprocessing steps can be implemented: bias field correction, intensity normalization, spatial normalization, skull stripping, and tissue segmentation. The inner cortical surface (matching the white matter/grey matter junction) and the outer cortical surface (matching the grey matter/cerebrospinal fluid interface), can then be extracted. Additionally or alternatively, a subcortical surface can also be extracted. The surfaces can be corrected for possible topological defects, inflated, and parameterized.

The extracted cortical surfaces (e.g., the inner and outer cortical surfaces of the left and right hemispheres) can be normalized by registering them to a template space, such as the MNI space (e.g., the MNI305 template, the ICBM152 template). This registration can be done by applying a volume-based, or other, affine registration to the surface vertices coordinates to spatially normalize the cortical surfaces and normalize brain volumes.

A surface-based registration is performed to establish a vertex-wise correspondence across individuals. As a non-limiting example, a non-rigid surface registration can be performed to improve cortical folding alignment (as determined by the curvature of the surfaces) between a subject and a surface template, which can result in distortion of the sulcal pattern. To preserve the initial sulcal folding pattern, surfaces can be rigidly registered to the surface template. In a trade-off between precision of cortical alignment across subjects and preservation of individual subjects' cortical folding pattern, this process prioritizes preservation of subjects' folding pattern.

Cartesian coordinates of the vertices (e.g., x, y, and z coordinates of the inner and outer cortical surfaces) in individual's native space can be registered to the template space (e.g., MNI space) by applying the volume-based affine transformation. The vertices can then be registered to the common surface space using a rigid surface-based transformation. Finally, vertices coordinates can be resampled to the surface template to decrease the number of vertices in the common surface space. This significant reduction in the number of vertices is beneficial to train neural networks or other machine learning algorithms much faster while maintaining anatomic precision. Additionally, registration to the surface template permits mapping the cortical areas relevant in the decision process across subjects.

Graph convolutional neural networks ("gCNNs") are a transposition of convolutional neural networks ("CNNs") to any graph, G. For example, letting G=(V,E,W) be a connected graph where V is a set of n vertices, E is a set of edges, and W is an $\mathbb{R}^{n\times n}$ adjacency matrix, such as $W_{i,j}>0$ if there is an edge between the nodes (e.g., vertices) i and j, and $W_{i,j}=0$ otherwise. An input signal, $F\in\mathbb{R}^{n\times m}$, to the graph can be defined such that the ith row of F is an m-dimensional vector assigned to the ith node of G.

The purpose of gCNNs is to process an input signal, F, mapped on a graph, G. The normalized graph Laplacian of G can be defined as:

$$L=I_n-D^{-1/2}WD^{-1/2} \quad (2);$$

where $I_n$ is the identity matrix of size n×n and D a diagonal degree matrix, such as $$D_{i,i}=\sum_j W_{i,j}.$$

The graph Laplacian is a real and symmetric matrix and, therefore, has a complete set of orthonormal eigenvectors, $u_l$, associated with eigenvalues $\lambda_l$, such as $Lu_l=\lambda_l u_l$. The eigenvectors can be the graph Fourier modes and the eigenvalues the frequency spectrum. This enables the formulation of the Fourier transform, $\hat{x}$, of a vector, x, mapped on the graph, G, as $\hat{x}=U^T x$, and its inverse as $x=U\hat{x}$, where $U=[u_0, u_1, \ldots, u_{n-1}]$. The convolution operator "*" can therefore be defined in the Fourier domain for two vectors, x and y, mapped on G such as $x*y=U(\hat{x}\cdot\hat{y})$, where "·" is the element-wise Hadamard product. As in Euclidean spaces, a filter can be expressed in the Fourier domain by a function, g, modulating the frequency spectrum to define y, the vector obtained by filtering x with g, by:

$$y=Ug(\Lambda)U^T x \quad (3)$$

with $\Lambda=\text{diag}([\lambda_0, \lambda_1, \ldots, \lambda_{n-1}])$. An efficient implementation of spectral filters, g, can be computed recursively from the Laplacian to avoid eigen decomposition, which may otherwise be computationally intensive. In addition, these filters have a K-order polynomial parametrization, therefore utilizing K parameters to define, and localized with support size K.

Figure 3:
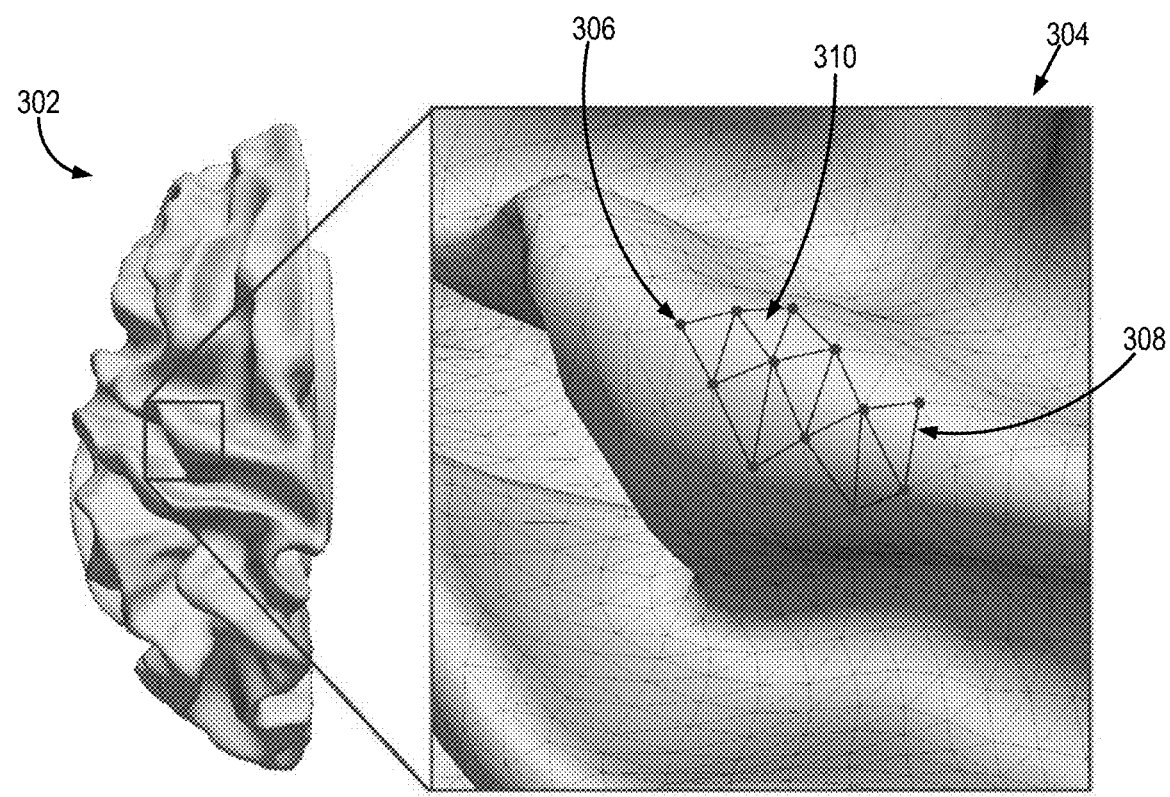
FIG. 3 shows an example brain surface and close up on a small part of the surface. Spatial relationships between each surface vertex are modeled via a graph. Nodes of the graph are surface vertices and edges of the graph are the links between the vertices. Edges are weighted as a function of their length. Node features, used as input of the gCNN, are each node's Cartesian coordinates in MNI space, resampled to the common surface space.

The graph provides the underlying structure of the data, in particular the relationships between its nodes, which is common to all subjects by construction. As shown in FIG. 3, in some examples the cortical surfaces 302 are triangulated meshes 304 composed of thousands or more vertices 306 per hemisphere connected by edges 308 to form triangles 310. The nodes of the graph, G, can be defined as the vertices 306 of the cortical surfaces 302, and the edges 308 are the links of the triangles 310, weighted as a function of the length of the link such as by Eqn. (1) described above. As also described above, the function F can be defined at the nodes of the graph, G. The input to the gCNN can therefore be the vertices coordinates registered to the MNI space (or other template space), registered and resampled to a common surface space. Therefore, each vertex in this example has six features if both the inner and outer cortical surfaces are used (x, y, and z coordinates of both white and pial surfaces), or three features if only the inner cortical surfaces are used (x, y, z coordinates of the white surface only). Additionally or alternatively, the input features can also be other characteristics of the image data that are mapped onto a mesh or other geometric framework that can be converted to a graph representation.

The pooling operation intends to downsample a graph and summarize information within a neighborhood, thereby providing a multiscale description of the data. In brief, setting the initial graph, G, and corresponding Laplacian matrix, L, to the level 0, multi-level graphs can be obtained by a successive node clustering, so that a coarse graph is obtained by grouping pairs of nodes of its parent graph. After B successive clusterings, this results in a set of graphs $G_0, G_1, \ldots, G_B$ with associated Laplacian matrices, $L_0, L_1, \ldots, L_N$ such as $n_k=2n_{k-1}$, where $n_k$ is the number of nodes of $G_k$. The efficiency of the pooling operation can be further increased by ordering the nodes so that node $p_i$ at level k+1 has the two parent nodes, $p_{2i}$ and $p_{2i+1}$, at level k.

Figure 4:
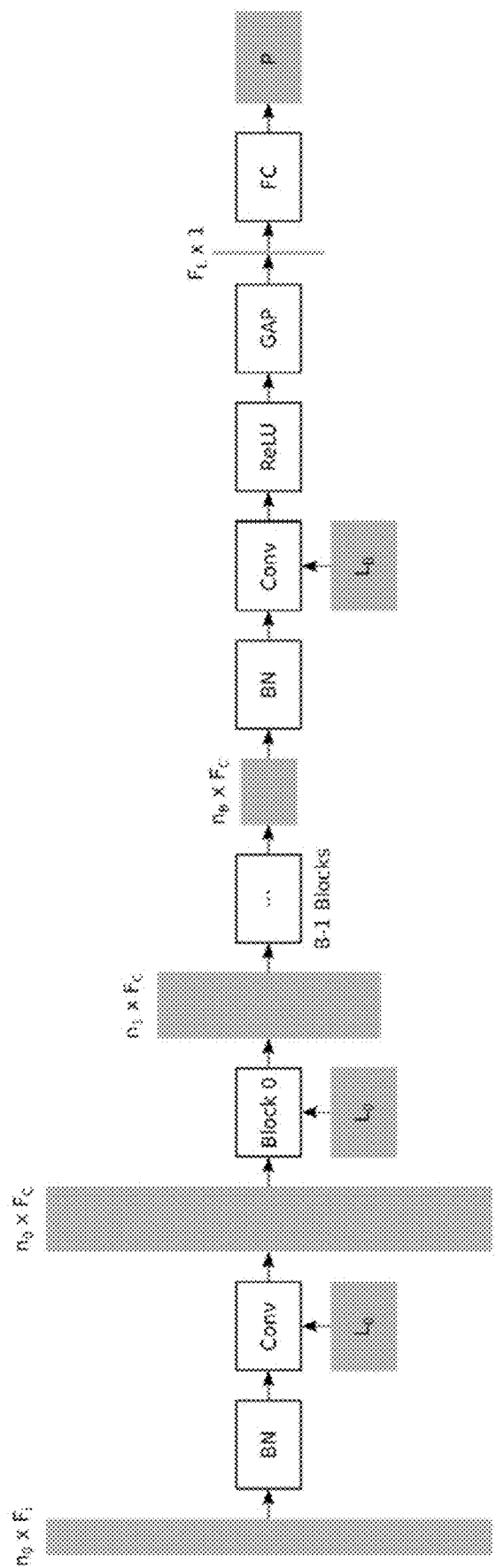
FIG. 4 shows an example graph convolutional neural network architecture that can be implemented in accordance with some embodiments described in the present disclosure.
Figure 5:
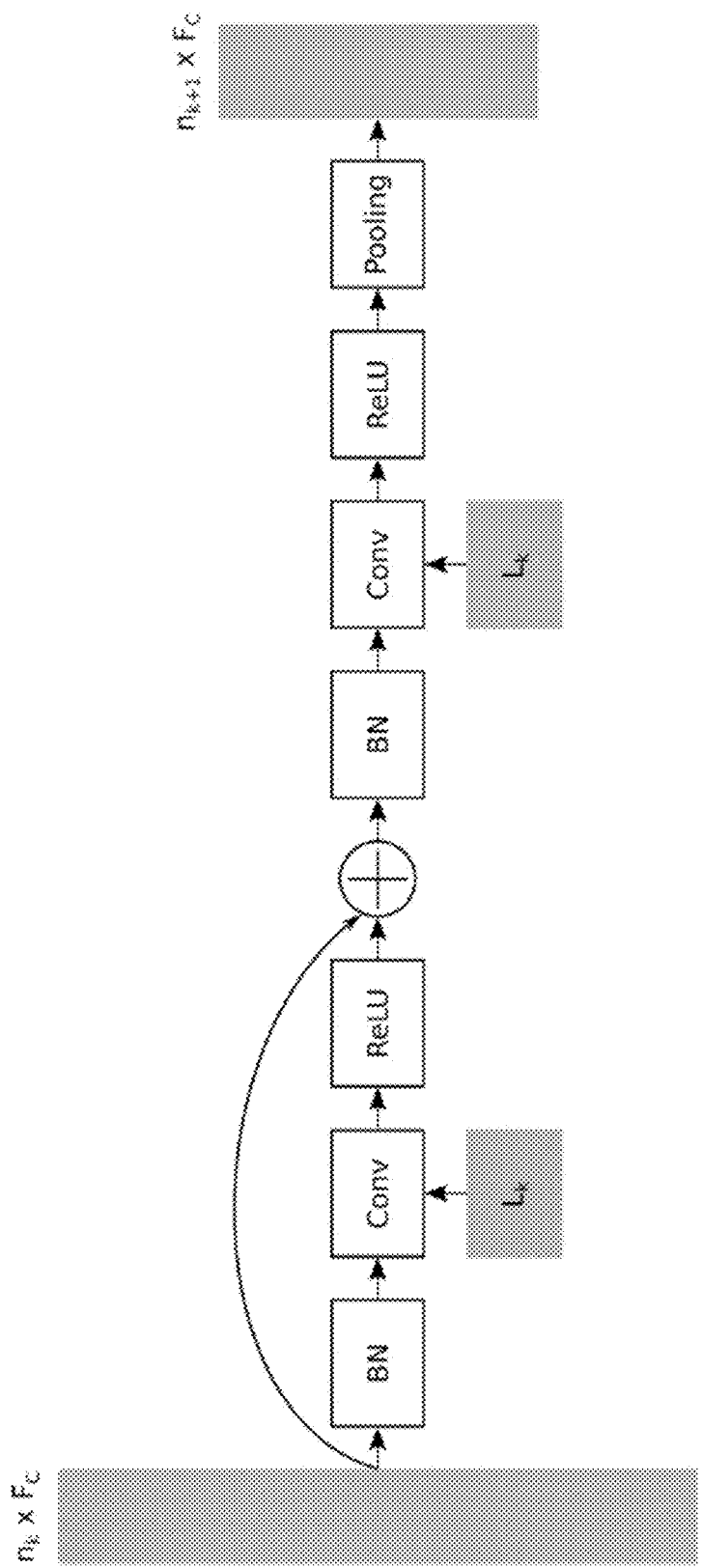
FIG. 5 is an example block of the graph convolutional network of FIG. 4.

The network architecture for an example gCNN that can be implemented in accordance with some embodiments described in the present disclosure is shown in FIG. 4. This example gCNN architecture explicitly refers to the input to make the overall network easier to optimize. A first batch normalization-graph convolution sequence extends the dimension of the input to the number of filters, $F_C$. Then, a series of B blocks are applied, each of them reducing the number of nodes with a pooling operation. This is followed by a batch normalization-graph convolution with $F_L$ filters, and activation function (e.g., a rectified linear unit ("ReLU")). Global average pooling ("GAP") can be used to summarize the $F_L$ feature maps into an $F_L$-length vector, linearly combined with the final fully connected (FC) layer. The architecture of the blocks used in the gCNN for FIG. 4 is illustrated in FIG. 5.

The topographic distribution of the most influential brain regions involved in the decision process can be mapped using a class activation map ("CAM") and/or regression activation map ("RAM"). These maps can be computed by interpolating the $F_L$-length feature vectors obtained before GAP to the initial vector length, $n_0$, and creating a weighted sum of these vectors according to the weights of the FC layer. These maps qualitatively highlight the brain regions involved in the gCNN's decision process.

In this example study, the aforementioned gCNNs were implemented to learn meaningful features using only surface meshes of the cortex for both a classification and regression task. In both tasks, four cortical surfaces including the inner and outer cortical surfaces from the left and right cerebral hemispheres were applied to a gCNN, leading to 6 input features per node (or only the inner cortical surfaces from each hemisphere which provided 3 features per node). The use of the inner cortical surface only prevents the network from deriving any information, even indirectly, from the cortical thickness, but instead forces the network to focus on morphologic descriptors of the cortical folding alone. In the case both the inner and outer cortical surfaces were used, the network can still extract morphologic descriptors of cortical folding, and is also given the possibility to extract descriptors of the inner cortical surfaces relative to the outer cortical surface, such as cortical thickness. Both of these training approaches can be alternatively used in order depending on whether it is desirable to include predictive information from cortical folding alone compared to richer information which may permit the network to infer additional measures of cortical morphology including cortical thickness. Additionally or alternatively, networks can be trained using the outer cortical surface only.

As a first experiment, the network was trained to classify sex. Training and validation were handled via a k-fold cross-validation approach with k=5, therefore the network was trained with 5128 instances and validated with 1282 independent instances. For this task, the loss function was cross-entropy, FC was set to 32 filters, the number of blocks B set to 4 and FL was set to 128. In addition, the polynomial order was set to 5 for all filters, the learning rate was set to 0.001 with an exponential decay 0.95 every 400 iterations, filter weights were L2 regularized to $5\times10^{-4}$, dropout 0.5 was applied to the fully connected layer, the batch size was 64 and the optimization was performed with Adam procedure. The number of trainable parameters was 62,758 when the input was either the inner or outer cortical surface, or 63,244 when both cortical surfaces were used as inputs.

Results were obtained for each 5 folds using either all four cortical surfaces (inner and outer cortical surfaces for both the right and left cerebral hemispheres) or the bilateral inner cortical surfaces only. Using all cortical surfaces, the gCNN was able to predict a subject's sex (using a binary classification scheme) with an average accuracy of 87.99%. Using only the bilateral inner cortical surfaces, average accuracy decreased only minimally to 85.23%.

Figure 6:
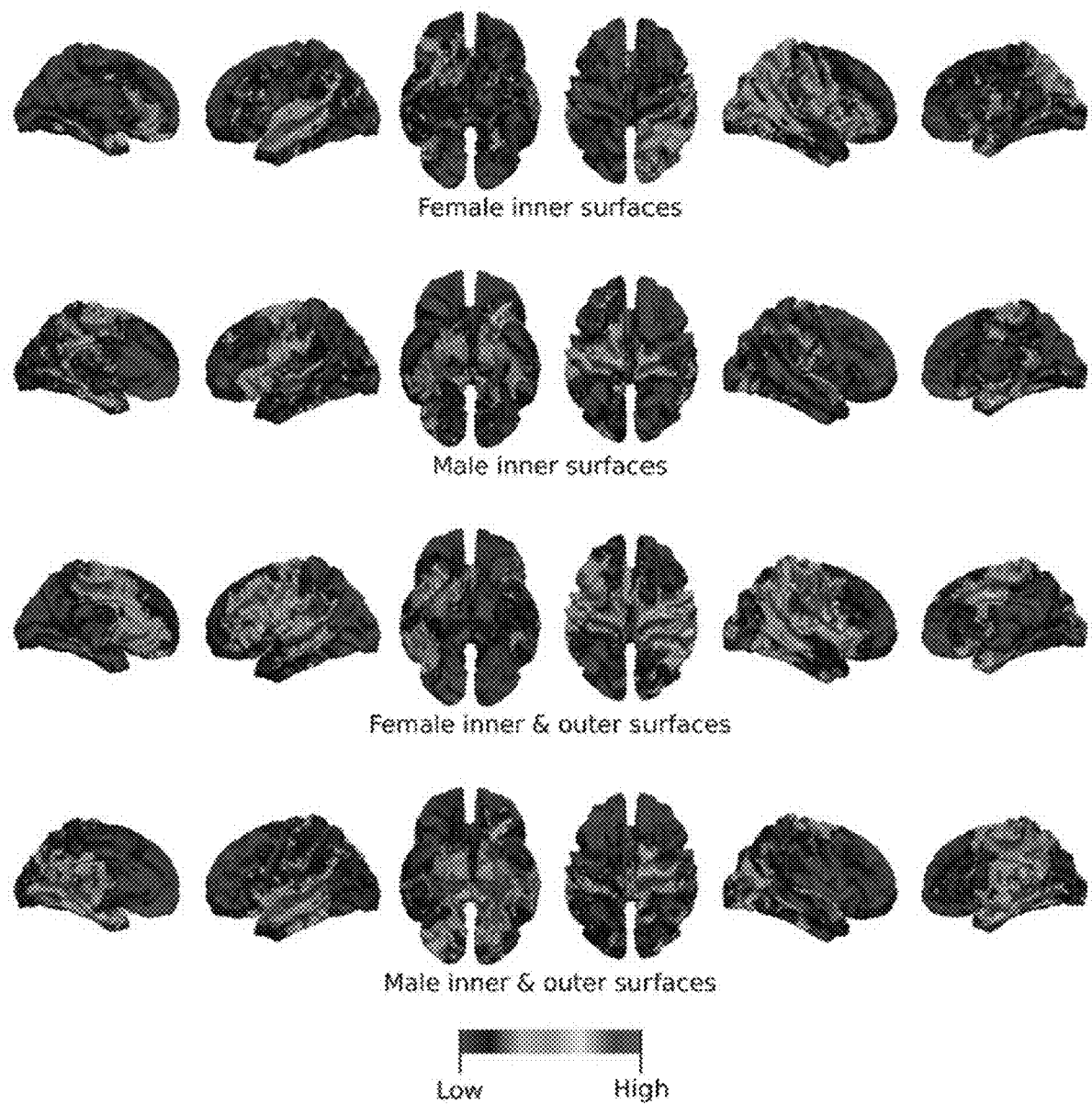
FIG. 6 shows average class activation maps ("CAMs") for correctly classified sex of individuals using either only the inner cortical surfaces, or the inner and outer cortical surfaces. The color indicates cortical areas with either low or high involvement in the decision.

FIG. 6 shows the CAMs averaged across correctly classified subjects for male and female. Overall, there was a modest amount of overlap between brain regions predicting binary sex classification when using the bilateral inner cortical surfaces compared to classification when using the bilateral inner and outer cortical surfaces.

When using the bilateral inner cortical surfaces only (i.e., only using morphologic features of the brain's sulcal/gyral folding pattern), the following brain regions were identified as predictive of female: left anterior cingulate cortex, left superior temporal gyrus, posterior left insula, right orbitofrontal cortex, entire right parietal cortex, right frontal operculum (including pars frontalis, pars triangularis and pars orbitalis) and the right insula.

When using the bilateral inner and outer cortical surfaces (i.e., morphologic features of the sulcal/gyral folding pattern and information regarding cortical thickness), the following brain regions were identified as predictive of female: left middle and anterior cingulate cortex, left superior temporal gyrus, left frontal operculum (including pars frontalis, pars triangularis and pars orbitalis), left posterior insula, right orbitofrontal cortex, right frontal operculum pars frontalis, right mid cingulate cortex, entire right parietal cortex and the right posterior insula.

When using the bilateral inner and outer cortical surfaces (i.e., morphologic features of the sulcal/gyral folding pattern and information regarding cortical thickness), the following brain regions were identified as predictive of male: left medial temporal tip, left medial temporooccipital junction, left superior temporal gyrus, left orbitofrontal cortex, left anterior insula, right medial paracentral lobule, right superior temporal gyrus, right lateral temporo-occipital junction and the right posterior cingulate cortex.

When using the bilateral inner cortical surfaces only (i.e., only using morphologic features of the brain's sulcal/gyral folding pattern), the following brain regions were identified as predictive of male: left medial paracentral lobule, left parahippocampal gyrus, left inferior frontal gyrus, left orbitofrontal cortex, left fusiform gyrus, left anterior insula, right medial paracentral lobule and the right medial temporal tip.

As a second task, the network was trained for age prediction using the same k-fold approach. The loss function was the mean squared error, FC was set to 32 filters, the number of blocks B was 7, FL was 16 and the polynomial order was 4 for all filters. The initial learning rate was 0.001 with an exponential decay 0.98 every 400 iterations, filter weights L2 regularization set to $1 \times 10^{-5}$, dropout 0.5 was applied to the FC layer, the batch size was set to 64 and optimization was done with the Adam method. In this setting, there were 75,702 trainable parameters when a single cortical surface was used, and 76,188 trainable parameters when both cortical surfaces were used.

Results were obtained for each 5 folds using either all four cortical surfaces (inner and outer cortical surfaces for both the right and left cerebral hemispheres) or the bilateral inner cortical surfaces only. Using only the inner bilateral cortical surfaces, Pearson's coefficient of correlation between the actual and predicted ages was 0.92 and the average absolute error was 4.91 years. Using all four cortical surfaces (bilateral inner and outer cortical surfaces), Person's coefficient of correlation was 0.93 and the average absolute error 4.58 years.

Figure 7:
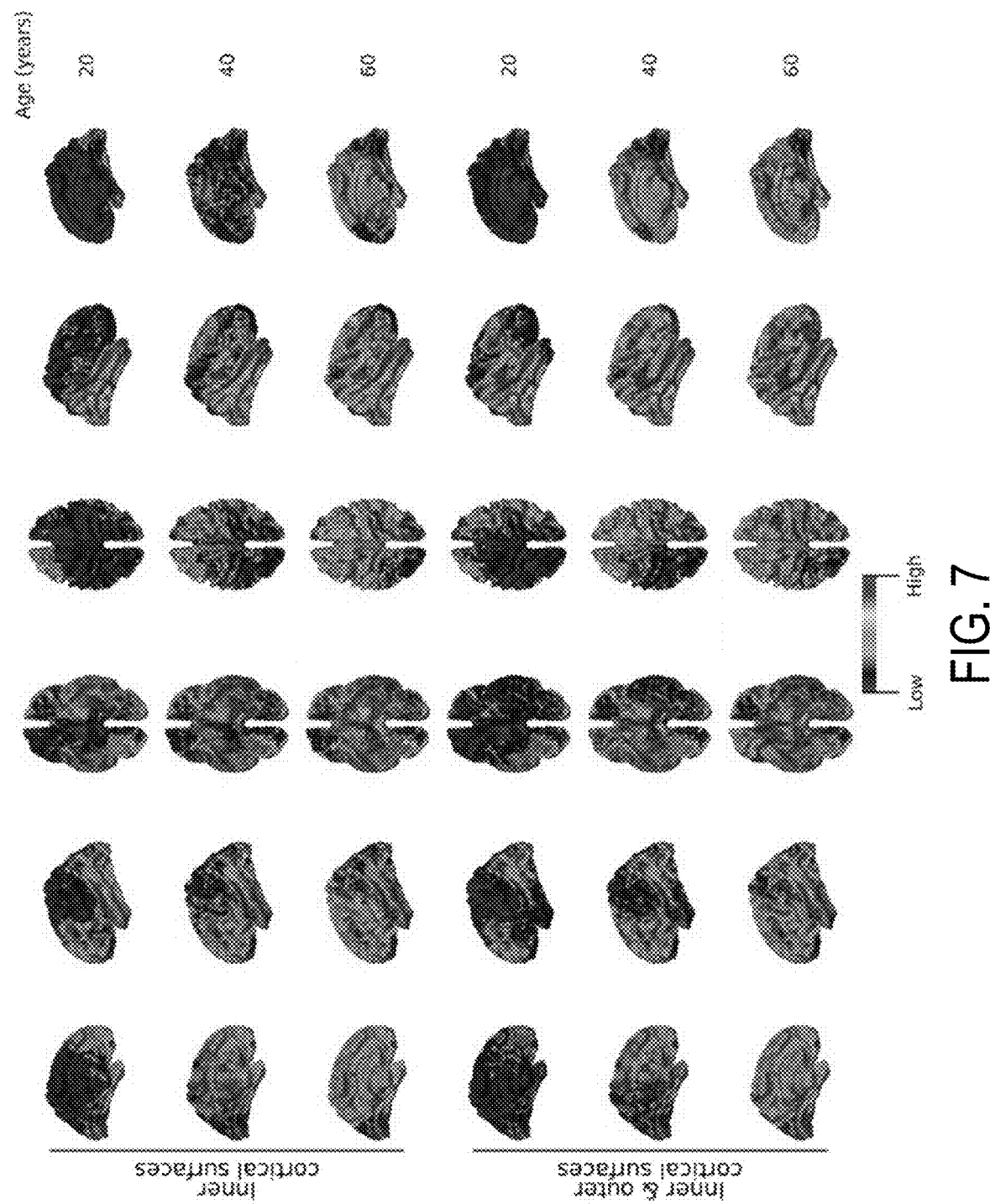
FIG. 7 shows regression activations maps ("RAMs") at ages 20, 40, and 60 years using the inner cortical surfaces, or both the inner and outer cortical surfaces. The color indicates cortical areas with either low or high involvement in the decision.

When using both the bilateral inner cortical surfaces only (i.e., only using morphologic features of the brain's sulcal/gyral folding pattern), or the bilateral inner and outer cortical surfaces (i.e., morphologic features of the sulcal/gyral folding pattern and information regarding cortical thickness), there was a general trend towards the temporal and parietal lobes in younger subjects with a progressive inclusion of the frontal lobes in older subjects. FIG. 7 shows example RAMs indicating the most influential brain regions for age prediction over a Gaussian sliding window (standard deviation 4 years) from 10 to 90 years old. In particular, FIG. 7 shows RAMs at ages 20, 40 and 60 years old.

In addition to this overall trend, younger subjects tended to be predicted correctly based on brain morphology alone (bilateral inner cortical surfaces only) primarily at the following brain regions: left medial prefrontal cortex, left dorsolateral prefrontal cortex, left inferior parietal lobule, left superior and inferior temporal gyri, right inferior parietal lobule (strong) and right occipital pole. Using a combination of brain morphology information and cortical thickness (bilateral inner and outer cortical surfaces), the left dorsolateral prefrontal cortex, left inferior parietal lobule, right inferior parietal lobule (strong) and right middle frontal gyri tended to be the most accurately predictive of young age.

Adult subjects, tended to be predicted correctly based on brain morphology alone primarily at the following brain regions: left medial paracentral lobule, left dorsolateral prefrontal cortex (to a lesser degree than in youth), left orbitofrontal cortex and the left prefrontal cortex including superior, middle and inferior frontal gyri). Using a combination of brain morphology and cortical thickness, the left medial paracentral lobule, left inferior parietal lobule, right greater than left orbitofrontal cortex and entire right frontal, temporal and parietal cortices over the cerebral convexity were found to be the most accurately predictive of adult age.

This example study implemented the data-driven approach described in the present disclosure for the analysis of cortical morphology using deep learning. In particular, the study implemented cortical surface models, obtained from T1-weighted magnetic resonance images, which are well-suited to represent the folded sheet nature of the cortical ribbon. The systems and methods described in the present disclosure constitute a departure from the classic volumetric analysis of brain imaging data.

For example, the systems and methods described in the present disclosure utilize explicit models of cortical morphology as inputs to a deep-learning network, generating output as a prediction and map of the most involved cortical areas in the prediction. This is in opposition with more traditional approaches where 3D or 2D-CNNs are fed with magnetic resonance images directly. In these more traditional settings, networks use gray-level voxel intensities (raw or preprocessed) from the magnetic resonance images which, by construction, cannot disentangle intensity changes from morphological changes. Advantageously, by feeding the networks described in the present disclosure with explicit and accurate models of cortical morphology, voxel intensity is disentangled from the cortical morphology, ensuring that findings relate only to the cortical shape.

Another advantage of the surface-based deep learning techniques described in the present disclosure is the natural two-dimensional representation of the cortical sheet, which is not only better suited to describe cortical topology but also helps to significantly reduce the dimensionality of the data. In the example study described above, the cortical ribbon was accurately modeled with 20,484 points, which represents fewer data points than a cubic grid of size $28^3$ and almost a 400-fold dimensionality reduction compared to standard whole brain 3D image of size $200^3$. Dimensionality reduction is advantageous for machine learning applications as it helps minimize undesired statistical properties associated with high dimensional data and can significantly decrease the computational burden during the learning process.

One of the many advantages of a gCNN approach to brain imaging analysis is its unique ability to produce topography distribution maps of brain areas identified to be the most involved in both classification and regression tasks. Despite deep learning's many notable strengths, one of its most significant drawbacks has been the inability to interpret the methods used by the network to make an accurate prediction. gCNN analysis offers the ability to circumvent this to some degree in its ability to generate activation maps following correct prediction by the network. These maps can be generated at either the subject or group level. When produced for a group, the maps can help understand the brain regions that are found to play a role in the correct prediction of the task at hand (in this case, correct prediction of age and sex), thus providing basic neuroscientific insights into the network's decision making process at the population level. These activation maps can provide information about which brain regions contributed to correct prediction and inform additional studies investigating what the features were in those locations that contributed to that correct prediction.

In another example, the systems and methods described in the present disclosure can be implemented to predict or otherwise characterize a condition of a subject's brain, such as a prediction or probability of whether the subject has or will develop a disease (e.g., Alzheimer's disease dementia) or another neurological condition. In this example, a spectral graph convolutional network is implemented, as described below in more detail.

Spectral-based graph convolution methods inherit ideas from a graph signal processing ("GSP") perspective. As described above, cortical surface data can be extracted or otherwise generated from image data and converted to graph representation data (e.g., undirected graphs) defined by a finite set of N vertices, V, and a corresponding set of edges, E, with scalar edge weights, $e_{ij}$, which are stored in the ith rows and jth columns of the adjacency matrix, $A \in \mathbb{R}^{N \times N}$. A graph's node attributes can be defined using the node feature matrix $X \in \mathbb{R}^{N \times F}$, where each column, $x_i \in \mathbb{R}^N$, represents the feature vector for a particular shared feature across each of the vertices, $v_i \in V$.

An emphasis in GSP is placed on the normalized graph Laplacian, $L=I_N-D^{-1/2} AD^{-1/2}$, where $I_N$ is the identity matrix and D is the diagonal matrix of node degrees, with $$D_{ii} = \sum_j A_{ij}.$$

The normalized graph Laplacian, L, can be factored via the eigen decomposition: $L=U \Lambda U^T$, as described above, where $U \in \mathbb{R}^{N \times N}$ is the complete set of orthonormal eigenvectors for L and $\Lambda = \text{diag}([\lambda_0, \lambda_1, \ldots, \lambda_{N-1}]) \in \mathbb{R}^{N \times N}$ is the corresponding set of eigenvalues. Given a spectral filter, $g_\theta$, defined in the graph's Fourier space as a polynomial of the Laplacian, L, and U orthonormality, each column, x, can be filtered via multiplication, such that, $$g_\theta *_G x = g_\theta(L)x = g_\theta(U \Lambda U^T)x = U g_\theta(\Lambda) U^T x \quad (4);$$

where $\theta \in \mathbb{R}^N$ are the parameters of the filter $g_e$ and $*_G$ is the spectral convolution operator. Furthermore, $U^T x$ is the graph Fourier transform ("GFT") of the graph signal x, $g_\theta(\Lambda)$ is a filter defined using the spectrum (eigenvalues) of the normalized Laplacian, L, and the left-sided multiplication with U is the inverse-GFT ("IGFT"). In this context, convolution is implicitly performed by using the duality property of the Fourier transform such that a spectral filter is first multiplied with the GFT of a signal, and then the IGFT of their product is determined.

In some embodiments, Chebyshev polynomials of the first kind can be used to approximate $g_\theta$ using the graph's spectrum, such that, $$g_\theta(\tilde{L}) = \sum_{k=0}^{K-1} \theta_k T_k(\tilde{L})$$

for the scaled Laplacian, $$\tilde{L} = \frac{2L}{\lambda_{max}} - I_N$$

where $\lambda_{max}$ is the largest eigenvalue in $\Lambda$ and K can be interpreted as the kernel size. Chebyshev polynomials of the first kind are defined by the recurrence relation, $$T_k(L) = 2\tilde{L}T_{k-1}(\tilde{L}) - T_{k-2}(\tilde{L})$$

where $T_0(\tilde{L})=I$ and $T_1(\tilde{L})=\tilde{L}$.

Using the FreeSurfer image analysis suite (http://surfer.nmr.mgh.harvard.edu/), magnetic resonance images can be denoised followed by field inhomogeneity correction, and intensity and spatial normalization. Inner cortical surfaces (interface between gray and white matter) and outer cortical surfaces (CSF/gray matter interface) can be extracted and automatically corrected for topological defects. Additionally, seven subcortical structures per hemisphere can be segmented (including amygdala, nucleus accumbens, caudate, hippocampus, pallidum, putamen, thalamus) and modeled into surface meshes using a tool that computes point-based models using a parametric boundary description for the computing of shape analysis, such as the SPHARM-PDM analysis tool (https://www.nitrc.org/projects/spharm-pdm).

Surfaces can be inflated, parameterized to a sphere, and registered to a corresponding spherical surface template using a rigid-body registration to preserve the cortical and subcortical anatomy. Surface templates can be converted to meshes using their triangulation schemes. A scalar edge weight, $w_{ij}$, can be assigned to connect vertices $v_i$ and $v_j$ using their geodesic distance, $\psi_{ij}$ (or other suitable distance metric), such that, $$w_{ij} = w_{ji} = \frac{1}{\sigma \sqrt{2\pi}} e^{-\frac{1}{2}\left(\frac{\psi_{ij}}{\sigma}\right)^2}. \quad (5)$$

Surface templates can be parcellated using a hierarchical bipartite partitioning of their corresponding mesh. Starting with their initial mesh representation of densely triangulated surfaces, spectral clustering can be used to define two partitions. These two groups can then each be separated yielding four child partitions, and this process can be repeated until the average distance across neighbor partitions is below a threshold (e.g., 2.5 mm). For each partition, the central node can be defined as the node whose centrality was highest and the distance across two partitions can be defined as the geodesic distance (in mm) across the central vertices. Two partitions are neighbors if at least one node in each partition are connected. Finally, partitions can be numbered so that partitions 2i and 2i+1 at level L have the same parent partition i at level L−1. Therefore, for each level a graph can be obtained such that the vertices of the graph are the central vertices of the partitions and the edges across neighboring vertices are weighted as in Eqn. (5). This serves as an advantage to ensure that no singleton is produced by pooling operations for the cortex and subcortical structures.

Vertex features can be defined as the Cartesian coordinates of the surface vertices in the subject's native space registered to the surface templates. Performing template registration as an additional preprocessing step can be done to reduce the complexity of the neural network architecture and to eliminate or otherwise significantly reduce the need of incorporating an "alignment" term to the cost function to optimize later.

Cortical vertices can be assigned six features: the x, y, and z coordinates of both the white matter ("WM") and gray matter ("GM") vertices in the native space (e.g., the inner and outer cortical surfaces, as described above). Similar to the cortex, subcortical vertices can have three features: their corresponding x, y, and z coordinates in the native space as well. To maintain the same number of features for all vertices per scan, the corresponding cortical and subcortical feature matrices can be block-diagonalized into a single node feature matrix per scan. Sample meshes are shown in FIGS. 8A-8D, which show the left hemisphere cortical surface (FIG. 8A), right hemisphere cortical surface (FIG. 8B), left hemisphere subcortical surface(s) (FIG. 8C), and right hemisphere subcortical surface(s) (FIG. 8D).

Figure 9:
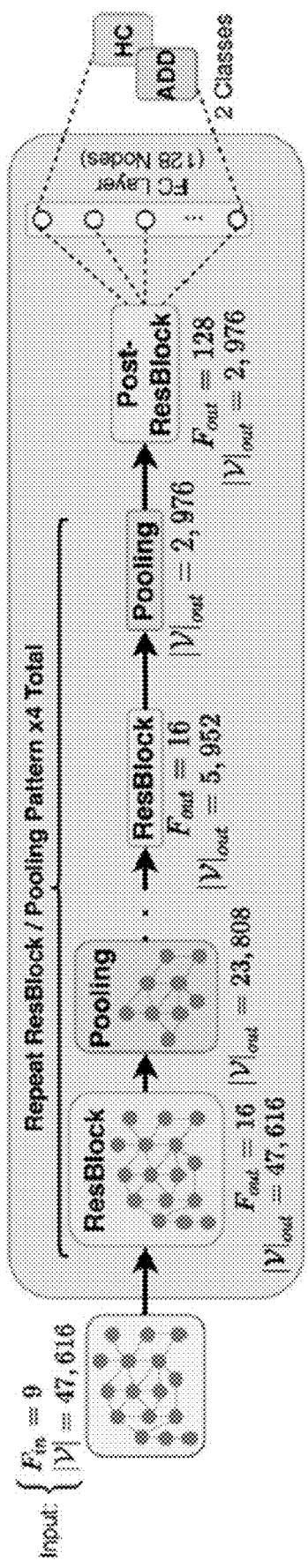
FIG. 9 is an example graph convolutional network ("GCN") architecture implementing residual connections and trained for the binary classification of Alzheimer's disease dementia.
Figure 10:
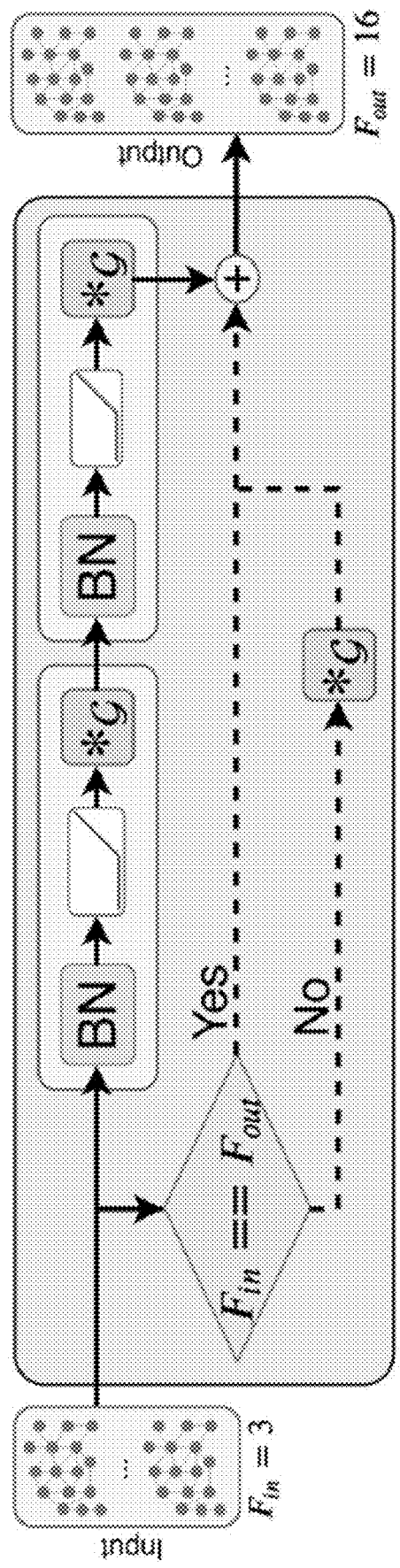
FIG. 10 shows an example ResBlock in the GCN architecture of FIG. 9.

The network architecture for an example neural network that can be implemented in accordance with some embodiments described in the present disclosure is shown in FIG. 9. This example network architecture implements residual connections within a graph convolutional network ("GCN"). These types of residual networks (ResNets) can be implemented using batch normalization ("BN") before a ReLU activation function, and followed by convolution as seen in FIG. 10. Using ResBlocks (FIG. 10), max-pooling operations, and a standard fully connected (FC) layer, the total architecture used in this example is shown in FIG. 9. An additional ResBlock, which may be referred to as a "post-ResBlock," can be introduced prior to the FC layer as a linear mapping tool to match the number of FC units.

Interpretability of neural networks can be provided via gradient-weighted class activation maps ("Grad-CAMs"). For example, images fed to a convolutional neural network and gradients for each class score (logits prior to softmax) can be extracted at the last convolutional layer. Using these gradients, a global average pooling ("GAP") operation for each feature map per class can be used to extract "neuron importance weights," $\alpha_c^{(k)} \in \mathbb{R}^{c \times k}$, whose formulation can be adapted for brain surface meshes, such that, $$\alpha_c^{(k)} = \frac{1}{N} \sum_n \frac{\partial y_c}{\partial A_n^{(k)}};$$

where $y_c$ corresponds to the class score of class, c, and $A_n^{(k)}$ refers to the value at vertex n for the kth feature map $A^{(k)} \in \mathbb{R}^N$. A set of neuron importance weights, $\alpha_c^{(k)}$, is extracted for each kth feature map, $A^{(k)}$, and projected onto them to get the class activation maps ("CAMs") such that, $$M_c = \text{ReLu}\left(\sum_k \alpha_c^{(k)} A^{(k)}\right) \in \mathbb{R}^N.$$

Following the pooling, CAMs can be upsampled to the same number of nodes as the input mesh for a direct "overlay" using an interpolation by going backward along the hierarchical tree used by the pooling operations.

In an example study, T1-weighted MRIs from the Alzheimer's Disease Neuroimaging Initiative ("ADNI") were selected with ADD/healthy control diagnosis labels given up to two months after the corresponding scan. The dataset used in this example study included 1,191 different scans for 435 unique subjects.

Meshes for each MRI were extracted following the process described above. The spatial standard deviation from Eqn. (5), σ, was set to 2 ad-hoc. The visual quality for each mesh was assessed manually via a direct overlay over slices of the corresponding MRI. Laplacians for the cortex and each subcortical structure were block-diagonalized to create one overall L representing a single mesh with multiple connected components. Extracted feature matrices for each sample were min-max normalized per feature to the interval [−1, 1] prior to feeding batches of data into the networks. The added zeros during block-diagonalization were ignored during each normalization step.

A dataset splitting function was implemented such that the distribution of labels was preserved amongst each set while also ensuring to avoid subject overlap. In this example, 20% of the samples were selected at random for the testing set. Of the remaining 80%, 20% of those were withheld as the validation set, while the remaining belonged to the training set. A 25-trial Monte Carlo cross-validation was performed using this data split scheme.

The architecture in FIG. 10 was implemented using 16 kernels per convolutional layer (not including the post-ResBlock), Chebyshev polynomials of order K=3, and pooling windows of size p=2. Four alternating ResBlock and pooling layers were cascaded as shown in FIG. 10 prior to the post-ResBlock. The number of units at the post-ResBlock and FC layer was 128. The GCN was optimized by minimizing a standard binary cross-entropy loss function, $$\mathcal{L} = -\frac{1}{N} \sum_{n=1}^{N} y_n \log(\hat{y}_n) + (1 - y_n)\log(1 - \hat{y}_n)$$

where $\hat{y}_n$ is the predicted class for the nth sample of N total samples and $y_n$ is the ground truth label for the same sample index, n.

Networks were trained in an example study using batches of 32 samples per step for 100 epochs in each Monte Carlo trial. The Adam optimizer was used with a learning rate of $5 \times 10^{-4}$ and a learning rate decay of 0.999.

Cross-validation included a multilayer perceptron ("MLP") classifier architecture, ridge classifier, and a 100-estimator random forest classifier. The MLP designed such that the number of hidden layers and parameters was the same as the GCNs. The GCN outperformed other standard classifiers not limited to graph methods on the example study dataset split.

Figures 11A, 11B, 11C, 11D, 11E, 11F, 11G, 11H:
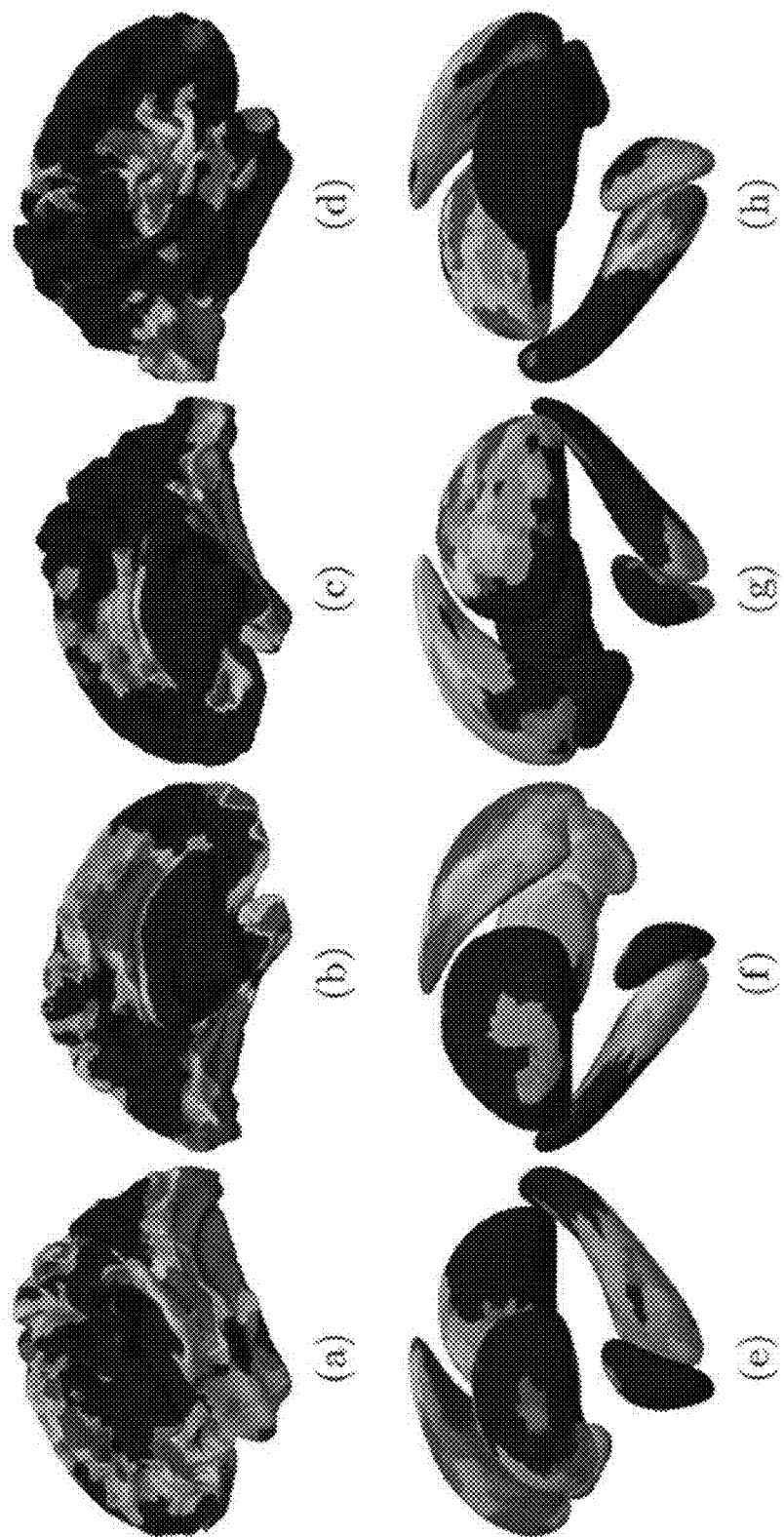
FIGS. 11A-11H show examples of average true prediction CAMs on a cortical template (top, FIGS. 11A-11D) and subcortical structures (bottom, FIGS. 11E-11H) including.

By employing Grad-CAM on the GCN, an average CAM was generated for true positive ("TP") predictions, as shown in FIG. 11. The CAM can be projected onto a cortical template or other cortical surface and/or subcortical structure templates or surfaces. The color scale highlights areas from least-to-most influential in TP predictions. The patterns in the CAM match previously described distributions of cortical and subcortical atrophy.

In this example study, the systems and methods described in the present disclosure were thus implemented for binary ADD clinical diagnosis and ROI visualization in TP predictions from cortical and subcortical surface meshes. Natural extensions of this example include expanding the classification problem to include additional classes (e.g., a third class from ADNI, mild cognitive impairment (MCI)). Additionally, having a 3D-volume-to-mesh dataset offers the potential for developing generative networks for performing the graph extraction preprocessing step described above. This will provide more autonomy and limit the need for the manual quality assessment ("QA") of meshes as a part of the processing pipeline.

In still another example, the systems and methods described in the present disclosure can be implemented to predict or otherwise characterize a condition of a subject's brain, such as a prediction or probability of whether the subject has or will develop a disease (e.g., Alzheimer's disease) or another neurological condition. In this example, a discriminative and generative spiral networks are implemented, as described below in more detail.

This example implementation provides a joint framework for improved in vivo disease classification using multiple subcortical structures in a single scan. A holistic view of brain subcortical anatomy is provided to demonstrate stronger discriminative performance with multiple brain structures. For AD in particular, correspondences across multiple structures can be more robust than studying one organ in isolation, especially in neuroimaging where segmenting multiple subcortical regions is possible from a single MRI volume. AD has also been identified as starting in localized brain regions (good for early detection) and progressively spreading to multiple brain regions (good for robust detection).

Discriminative spiral networks can be used for improved AD (or other disease or condition) classification on brain surface meshes. An improvement in accuracy, precision, recall, and F1-score can be realized by using spiral convolution on brain surface meshes for AD (or other disease or condition) classification. The discriminative spiral network can also outperform alternative shape-based descriptor approaches, which operate on intermediate shape representations, such as point clouds.

Mesh Grad-CAM adaptations can be used to provide visual reasoning in localized regions-of-interest ("ROIs") on mesh manifolds that drive TP predictions in AD (or other disease or condition) classification. Grad-CAM can be useful for localizing ROIs on meshes for TP predictions from GCNs, as described above. Although a different convolution operator is used in the spiral networks described in this embodiment, learned feature maps are still attainable from convolutional layers for generating class activation maps ("CAMs") onto input mesh surfaces. These CAMs are a visual interpretation of regions on the along the surface of subcortical structures whose shape is indicative of TP AD (or other disease or condition) predictions by the spiral networks. The CAMs obtained in an example study draw direct correspondences with brain shape deformations tightly correlated with AD pathology.

Conditional generative spiral networks can be used for low-dimensional representation learning on brain surface mesh manifolds with diagnostic priors. A generative conditional variational autoencoder ("CVAE") model is able to learn low-dimensional discriminative representations of surface mesh inputs, which can then be evaluated against the discriminative network and prior baseline methods. The morphological effects of conditioning on AD can also be analyzed and supported by multiple reports on the neuroanatomical changes in AD progression.

The input domain of the cortical surface and/or graph representation data is represented using triangular mesh manifolds, $M=(\mathcal{V}, \varepsilon, \mathcal{F})$ for the corresponding finite set of vertices, edges, and faces for each mesh. In graph signal processing, meshes can be treated as undirected graphs, where a feature vector of F features at vertex i is defined by a row vector $x_i \in \mathbb{R}^F$ for N vertices. To encapsulate all of the shared features on the vertices of a single mesh, a vertex feature matrix, $X \in \mathbb{R}^{N \times F}$ can be used.

The shared features on the vertices of the input meshes are the corresponding x, y, and z coordinates (three features total) of each vertex in the corresponding subject's native 3D space. The meshes are registered to a common mesh template (e.g., a template of subcortical structures). The meshes can use a shared topology (e.g., same number of vertices/edges). However, the positions of vertices will generally vary across samples, thereby representing a span of different 3D morphology for each sample using the same template of connectivity. An analogous set-up with Euclidean data could be a 3D array of voxels, where the feature at each voxel is the corresponding location of the voxel in the subject's native space.

Beginning with the obtained T1-weighted MRIs, the FreeSurfer image analysis tool (or another suitable image analysis tool) can be used to denoise each scan, then followed by B1-field homogeneity corrections and intensity/spatial normalization. Seven subcortical structures per hemisphere can be segmented (including amygdala, nucleus accumbens, caudate, hippocampus, pallidum, putamen, thalamus) and modeled into surfaces using SPHARM-PDM, as described above.

Next, surfaces can be inflated, parameterized to a sphere, and registered to a common spherical surface template using a rigid body registration to preserve the subcortical anatomy. Then, surface templates can be converted to triangular meshes following a triangulation scheme. A scalar edge weight, $w_{ij}$, can be assigned to each edge, $e_{ij}$, connecting vertices i and j, using their geodesic distance, $\psi_{ij}$, along the surface such that, $$w_{ij} = w_{ji} = \frac{1}{\sigma\sqrt{2\pi}} e^{-\frac{1}{2}\left(\frac{\psi_{ij}}{\sigma}\right)^2}$$

for $\sigma=2$ selected ad-hoc.

As described above, surface templates can be parcellated using a hierarchical bipartite partitioning of their corresponding mesh. Beginning with the initial mesh representations of densely triangulated surfaces, spectral clustering can be used to define two partitions. These two partitions can then each be separated, yielding four child partitions, and repeated so forth. This process can be repeated until the average distance across neighboring partitions was a selected distance (e.g., 2.5 mm). Given one partition, the central vertex of a partition can be defined as the vertex whose centrality was the highest. The distance across two partitions can be defined as the geodesic distance (in mm)

across the central vertices of each partition. Two partitions are considered neighbors if at least one vertex in each partition are connected.

Finally, as described above, partitions can be numbered so that partitions 2p and 2p+1 at level L, have the same parent partition p at level L−1. Therefore, for each level a mesh can be obtained such that the vertices of the mesh are the central vertices of the partitions and the edges across neighboring vertices are weighted using the scalar edge weights, $w_{ij}$, described above. This helps ensure that no singleton is produced by mesh coarsening operations for the subcortical structures.

FIGS. 12A and 12B illustrate examples of spiral sequences on 3D morphable brain meshes. Given an arbitrary triangular mesh and an arbitrarily selected vertex that can be referred to as a center vertex, a spiral sequence can be naturally enumerated by following a spiral pattern around the center vertex. First, a spiral orientation is fixed (clockwise or counter-clockwise) and a random starting direction is selected from the center vertex. As a non-limiting example, orientations for all spiral generations can be fixed to counter-clockwise and an arbitrary starting direction with respect to each vertex can be used.

In a specific, but non-limiting, example, a k-ring and a k-disk around a center vertex v is defined as:

$$0\text{-ring}(v) = \{v\},$$
$$k\text{-disk}(v) = \bigcup_{i=0,\ldots,k} i\text{-ring}(v),$$
$$(k+1)\text{-ring}(v) = \mathcal{N}(k\text{-ring}(v)) \setminus k\text{-disk}(v),$$

where $\mathcal{N}(V)$ is the set of all vertices adjacent to any vertex in set V. A spiral sequence of length $\ell$ at vertex v can be defined as $S(v, \ell)$; a canonically ordered set of $\ell$ vertices from a concatenation of k-rings. Only part of the last ring is concatenated in this definition in order to ensure a fixed-length serialization. Formally, the spiral sequence can be defined as:

$$S(v, \ell) \subset \{0\text{-ring}(v), 1\text{-ring}(v), \ldots, k\text{-ring}(v)\}.$$

The spiral sequences show significant advantages to a high-level feature representation for each vertex in a consistent and robust way when spirals are frozen during training. By this, it is meant that spiral sequences are generated only once for each vertex on the template mesh, instead of randomly generated sequences for every vertex per epoch. Because the 3D mesh samples used in the described embodiments are all registered to a common template topology, the same spiral sequences can be used for every sample. By design, this automatically generates the topology of the convolutional filter on each vertex of the template mesh, analogous to the assumed rectangular topology of convolutional filters with standard 2D Euclidean CNNs. In other examples, different spiral sequences may be generated for different samples.

CNNs applied on 2D/3D images defined on standard Euclidean grids are designed using 2D/3D rectangular convolutional kernels that slide across the images and map $F_{in}$ input feature maps to $F_{out}$ output feature maps. An extension of this application on data types in irregular domains, such as graphs, can be expressed using neighborhood aggregation or message passing schemes, as examples.

Using the convention described above, with $x_i^{(k-1)} \in \mathbb{R}^{F_{in}}$ denoting the feature vector of $F_{in}$ features at vertex i and $e_{i,j} \in \mathbb{R}^{E_{in}}$ denoting the (optional) $E_{in}$ features on edge $e_{i,j}$ connecting vertex i to vertex j at layer (k−1), message passing neural networks can be defined such that, $$x_i^{(k)} = \gamma^{(k)}(x_i^{(k-1)}, \square_{j \in \mathcal{N}(i)} \phi^{(k)}(x_i^{(k-1)}, x_j^{(k-1)}, e_{i,j}^{(k-1)}))$$

where $\square$ represents a differentiable permutation-invariant operation (i.e. sum, mean, or max), and $\gamma^{(k)}$ and $\phi^{(k)}$ denote differentiable kernel functions such as multi-layer perceptrons ("MLPs"). CNNs defined for data types that exist in standard Euclidean grids have a clear one-to-one mapping. However for data types in irregular domains, such as graphs, correspondences can be defined using neighborhood connectivity for each vertex and weight matrices dependent on the kernel functions, $\gamma$ and $\phi$, at each layer. Using the spiral sequence serialization discussed above, convolution on meshes can be defined in an equivalent canonical manner to Euclidean CNNs that is anisotropic by design. The spiral convolution operator can be defined as, $$x_i^{(k)} = \gamma^{(k)}\left(\|_{j \in S(i,\ell)} x_j^{(k-1)}\right);$$

where $\gamma$ denotes MLPs and $\|$ is the concatenation operation applied on the shared features of the vertices of spiral sequence $S(i, \ell)$ centered at vertex i.

The dilated extension of spiral convolution using the dilated spiral sequence (depicted in FIG. 12B) can also be applied to meshes by uniformly sub-sampling during spiral generation, with the preprocessing parameter, d, denoting a uniform sampling of every d−1 vertices along the spiral sequence until $\ell$ vertices are selected.

Traditional Euclidean CNNs can use a hierarchical multiscale learning structure, typically employed for learning global and local context, using a combination of convolutional and pooling/up-sampling layers. To mimic this behavior, mesh sampling/coarsening operators that define analogous down-sampling and up-sampling of mesh vertices within a neural network can be used.

As described above, vertex feature matrices for meshes with N vertices and F shared features can be denoted $X \in \mathbb{R}^{N \times F}$. As a non-limiting example, 3D mesh samples can use F=3 input dimensionality; however, convolutions applied on mesh features within the neural network can result in features with different dimensionality.

The in-network down-sampling of a mesh, with N vertices, can be performed using the down-sampling matrix, $D \in \{0,1\}^{M \times N}$ and up-sampling with $U \in \mathbb{R}^{N \times M}$ for N>M. The downsampling matrix, a sparse matrix, can be obtained by contracting vertex pairs iteratively that maintain surface error approximations using quadric matrices. The vertices of the down-sampled mesh are a subset of the original mesh's vertices, $\mathcal{V}_d \subset \mathcal{V}$. Each element of $D(p,q) \in \{0,1\}$ denotes whether the qth vertex is kept during down-sampling, with $D(p,q)=1$, or otherwise discarded with $D(p,q)=0$, $\forall p$.

To remain lossless, the up-sampling operator can be built during the generation of the down-sampling operator. Vertices retained during down-sampling are kept for up-sampling such that $U(q,p)=1$ iff $D(p,q)=1$. Vertices $q \in \mathcal{V}$ that are discarded during downsampling, $D(p,q)=0$, $\forall p$, can be mapped into the downsampled triangular mesh surface by using barycentric coordinates.

For example, this can be done by projecting q into the closest triangle (of vertices i, j, and k) of the down-sampled mesh surface, denoted by $\tilde{p}$, and determining the barycentric coordinates, $\tilde{p}=w_i i+w_j j+w_k k$, where i, j, $k \in \mathcal{V}$ and $w_i+w_j+w_k=1$. Using these weights, U can be updated such that, $U(q,i)=w_i$, $U(q,j)=w_j$, $U(q,k)=w_k$;

otherwise, $U(q,l)=0$.

Figure 13:
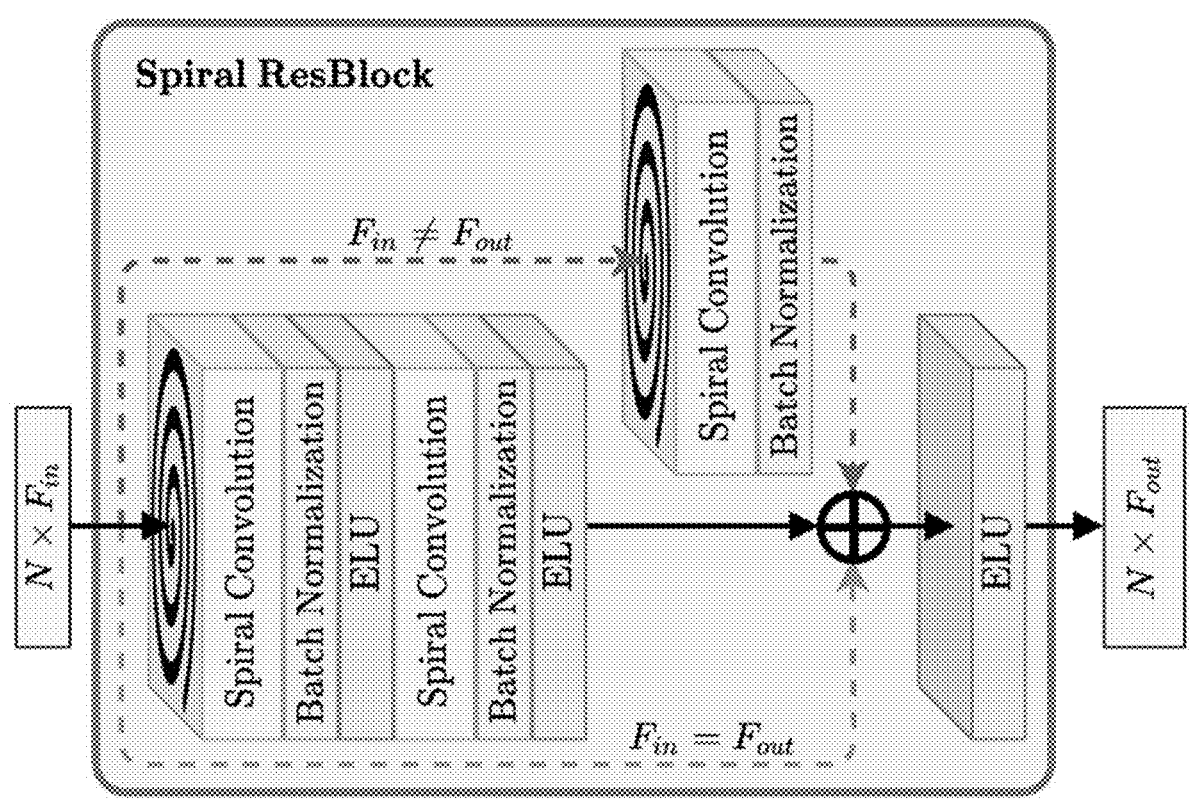
FIG. 13 shows an example residual learning block (ResBlock) module used in a spiral-based network architecture. Batch normalization (depicted in orange) is applied after spiral convolution (depicted in yellow). The top (red) branch of the ResBlock uses spiral convolution followed by batch normalization as an identity linear mapping tool to map the $F_{in}$ features of the input vertices to the $F_{out}$ features acquired by the main branch. Otherwise, the input of the ResBlock is added to the main branch output (green). An element-wise ELU function is used within the hidden layers and as the final activation of the ResBlock.

The features on the vertices retained from a down-sampling operation for the new mesh can be obtained via sparse matrix multiplication in, $Y=DX \in \mathbb{R}^{M \times F}$ for $X \in \mathbb{R}^{N \times F}$. In a synonymous way, the vertices on the output mesh of an up-sampling operation can be obtained as an inverse operation to down-sampling via the sparse matrix multiplication, $X=UY \in \mathbb{R}^{N \times F}$ Like some of the examples described above, a residual learning architecture composed of residual learning blocks (ResBlocks) can be implemented in the described embodiments. An example of such ResBlocks is shown in FIG. 13. These ResBlocks function by adding the output from a previous block to the output of the current block. This methodology allows for the training of deeper neural network architectures, with the intuition that adding more layers allows for progressively learning more complex features within the architecture.

A spiral convolutional layer maps $F_{in} \to F_{out}$ features for every vertex in the input mesh using MLPs applied on the spiral sequence, $S(i, \ell)$, of each vertex, i. Analogous to traditional convolution with padding to preserve the size of input feature maps, spiral convolution on meshes also preserves dimensionality since $S(i, \ell)$ is defined for every input vertex. Therefore, the number of vertices, N, is still preserved in the output vertex feature matrix, $X_{out} \in \mathbb{R}^{N \times F_{out}}$.

Batch normalization ("BN") is used after each spiral convolution operation within the ResBlocks as a way to standardize the inputs to layers within the network.

A notable hyperparameter for training deep networks is the choice of activation function for the hidden layers and output layer. As a non-limiting example, the rectified linear unit ("ReLU"), defined as $ReLU(x)=x^+=\max(0,x)$ can be used. Deep learning architectures using ReLU can sometimes be prone to suffering from a "dying ReLU" problem in which hidden layer outputs heavily saturate to zero, leading to zero-valued gradients and thereby making learning more difficult. This can be circumvented by using an exponential linear unit ("ELU") activation function defined as, $$ELU(x) = \begin{cases} x, & \text{if } x > 0 \\ \alpha(e^x - 1), & \text{if } x \leq 0 \end{cases}$$

for $\alpha=1$ as an example.

Figure 14:
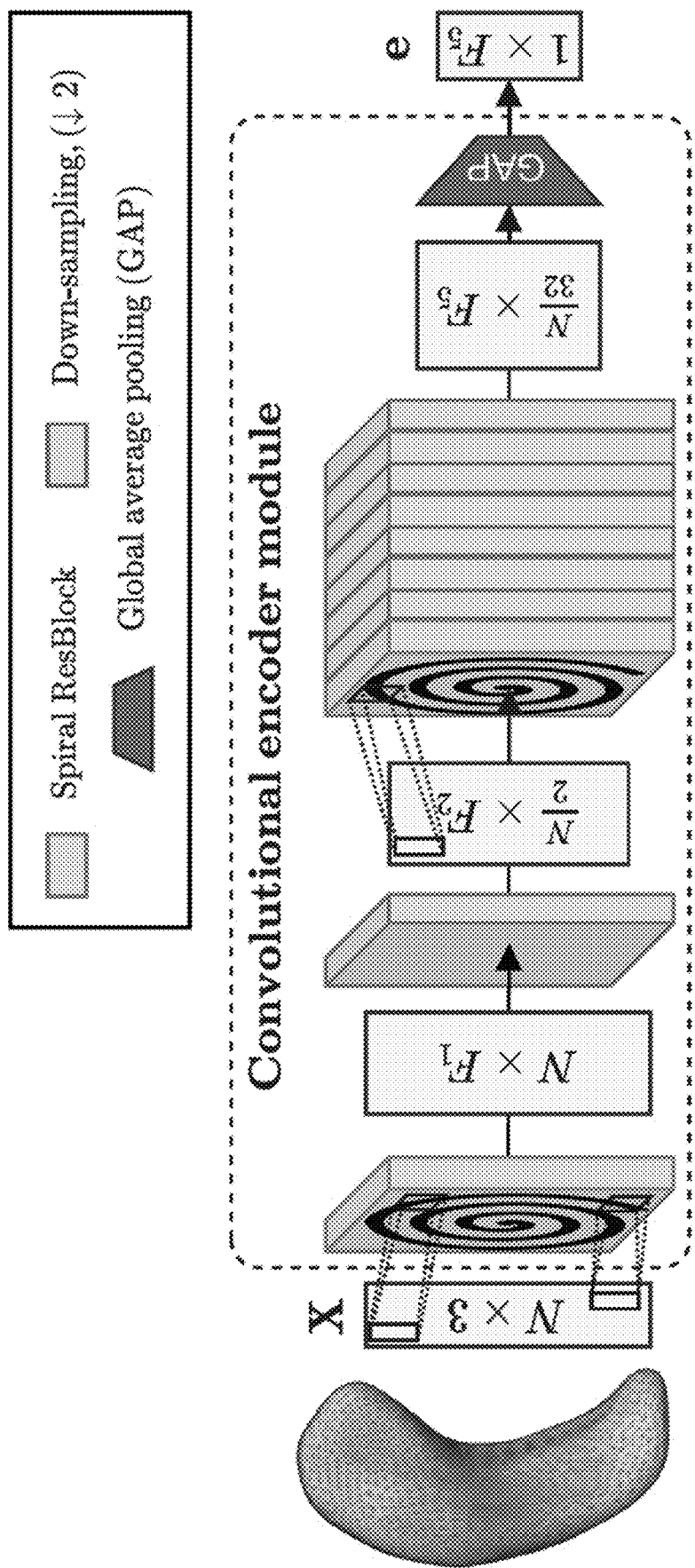
FIG. 14 is an example convolutional mesh encoder module made up of a sequential stack of alternating spiral convolution and down-sampling layers. The ith ResBlock $F_i$ maps $F_i$ features onto the vertices of the respective input. Each down-sampling layer coarsens the input vertex count down by a factor of 2. After the final down-sampling layer, global-average pooling (GAP) is applied over the vertex dimension to reduce the output embedding down to $\mathbb{R}^{F_5}$.

Using ResBlocks and mesh down-sampling, as described above, a convolutional encoder module used in an embodiments of a discriminative and generative spiral networks can be constructed, such as the convolutional encoder module shown in FIG. 14. As illustrated, input feature matrices are embedded to $\mathbb{R}^{F_5}$ latent vectors using the encoder defined as the sequential stack:

$\{ResBlock(\ell_1, d_1, F_1) \to MS(\downarrow 2) \to ResBlock(\ell_2, d_2, F_2)$
$\to MS(\downarrow 2) \to \ldots \to ResBlock(\ell_5, d_5, F_5) \to MS$
$(\downarrow 2) \to GAP_N\}$ Where $\ell_r$, $d_r$, and $F_r$ are the spiral lengths, dilation, and number of filters for all convolutional layers with respect to the rth ResBlock; $MS(\downarrow 2)$ indicates mesh-sampling down by a factor of 2 (down-sampling); and $GAP_N$ is the global average pooling operation.

On meshes, $GAP_N$ can be viewed as an averaging operation over the node dimension, as depicted in FIG. 14. Note that since the input mesh is down-sampled 5 times within the module, each time by a factor of 2, the number of vertices after the final down-sampling operation is $$\frac{N}{2^5} = \frac{N}{32}.$$

This module is used as the first step for both the discriminative and generative networks, as will be described below in more detail.

Figure 15:
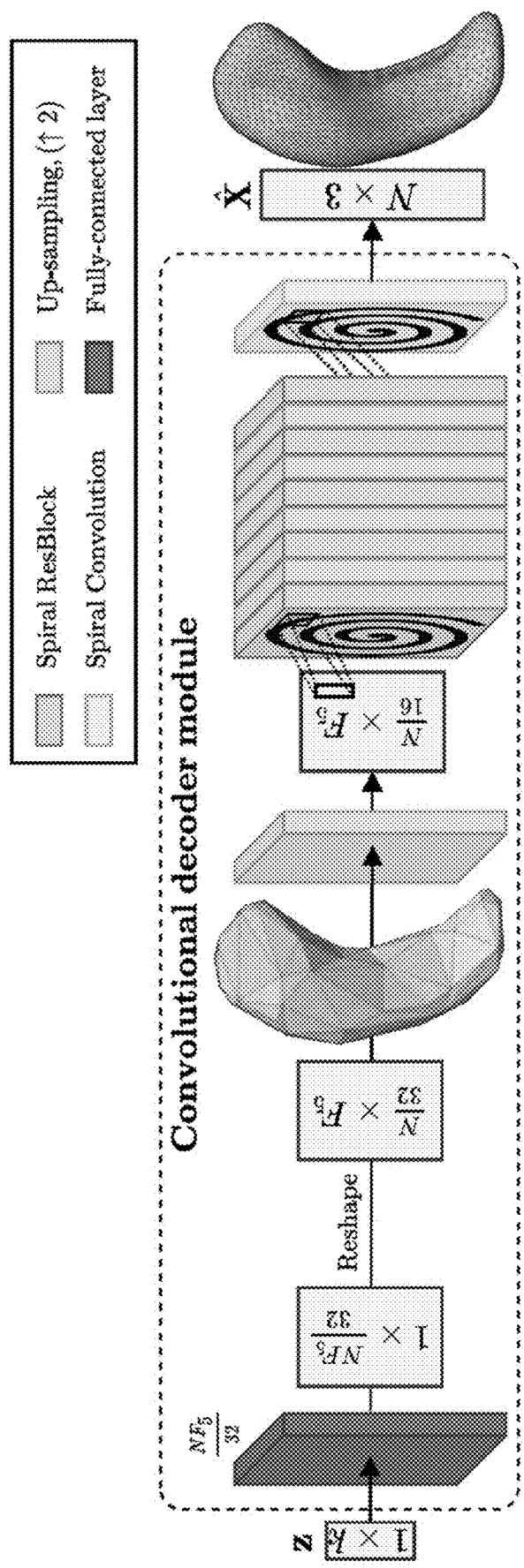
FIG. 15 is an example mesh decoder module, which first uses a FC layer and reshaping to map the input vector to a feature matrix for meshes at the coarsest level. Alternating up-sampling and ResBlock layers are used after. An additional spiral convolutional layer with 3 filters and no activation function is used to project the penultimate N×$F_1$ feature matrix back to N×3 for the respective 3D mesh reconstruction.

The convolutional mesh decoder module, depicted in FIG. 15, applies a synonymous backwards transformation of the encoder module described above with respect to FIG. 14. Following FIG. 15 and starting with an arbitrary vector $z \in \mathbb{R}^k$, first a fully-connected (FC) layer maps $$z \to \mathbb{R}^{\frac{NF_5}{32}}.$$

This output is then reshaped to get a feature matrix in $$\mathbb{R}^{\frac{N}{32} \times F_5},$$

representing the $F_5$ features on the $$\frac{N}{32}$$

vertices at the coarsest level of the meshes. The rest of the decoder module is defined as the sequential stack:

$\{MS(\uparrow 2) \to ResBlock(\ell_5, d_5, F_5) \to MS(\uparrow 2) \to Res$-
$Block(\ell_4, d_4, F_4) \to \ldots \to MS(\uparrow 2) \to ResBlock($
$\ell_1, d_1, F_1) \to SpiralConv(\ell_1, d_1, 3)\}$ Here $\ell_r$, $d_r$, and $F_r$ are the same corresponding values used in the encoder module. An additional spiral convolutional layer (SpiralConv) with 3 filters is used at the end (with no activation) to obtain the reconstruction, $\hat{X} \in \mathbb{R}^{N \times 3}$, with 3 features per vertex (corresponding x, y, z coordinates). This module is utilized within the generative network described below, where the task is to output 3D meshes.

Figure 16:
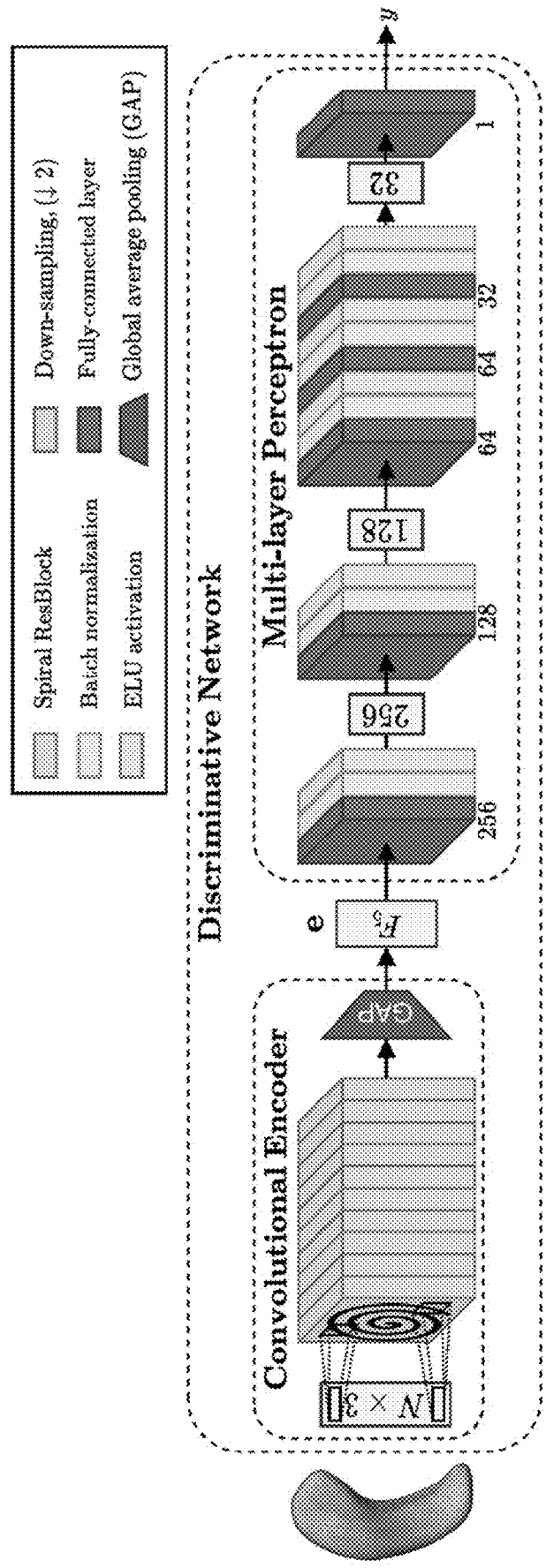
FIG. 16 is an example end-to-end discriminative spiral network given a 3D mesh input with feature matrix X∈ $\mathbb{R}^{N\times 3}$. Batch normalization is used after each MLP layer, followed by an ELU activation. Given the output of the convolutional encoder, the MLP predicts the target, y, from the embedding for a particular sample. For binary classification, a sigmoid function can be applied after the final layer to output a probability for each sample.

A discriminative network is constructed using the encoder module (FIG. 14) in series with an MLP that uses BN and an ELU activation function after each FC layer, as depicted in FIG. 16. The goal of this network is to learn mesh features given an input feature matrix, $X \in \mathbb{R}^{N \times 3}$, and a spiral convolutional operator that exploits the locally-Euclidean topology of 3D mesh manifolds. These learned mesh features are then global-average pooled and used within an MLP for predicting the target variable, y.

As a non-limiting example, the discriminative network can be used for binary classification. In these instances, the following sigmoid function can be applied to the predicted targets to get the probability of a positive label given the corresponding 3D mesh manifold, $$\sigma(y) = \frac{1}{1 + e^{-y}}.$$

For binary classification tasks such as disease prediction, the positive binary label, (1), pertaining to the pathology, is typically the positive class in opposition to the healthy control label, (0). The discriminative network can be trained in an end-to-end supervised manner by optimizing a standard binary cross-entropy ("BCE") loss, $$\mathcal{L}_{BCE} = -\frac{1}{B}\sum_{i=1}^{B}(y_i \log(\hat{y}_i) + (1 - y_i)\log(1 - \hat{y}_i))$$

where $y_i$ and $\hat{y}_i$ are the ground-truth labels and predicted probabilities (output of sigmoid), respectively, for a given sample, i, in a batch of B samples.

Figure 17:
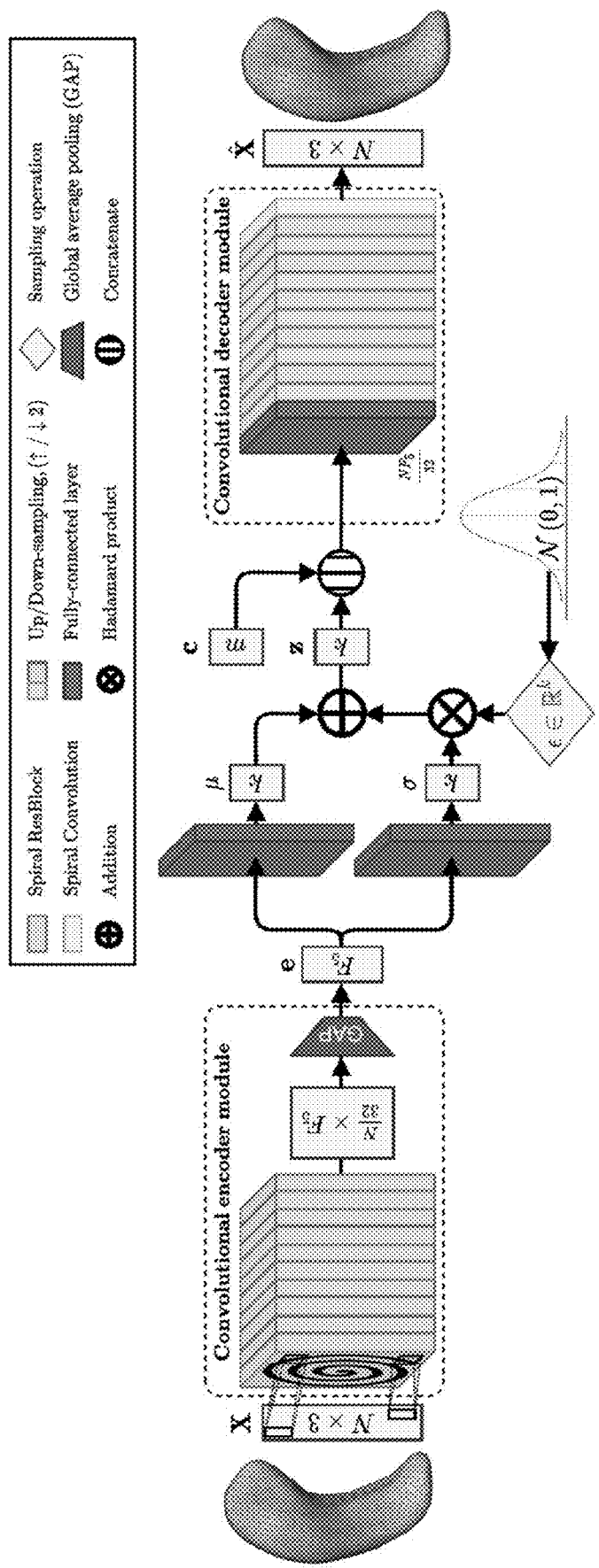
FIG. 17 is an example end-to-end generative model based on spiral convolutional CVAE architecture. During inference, a mesh sample is first encoded to e∈$\mathbb{R}^{F_5}$, using the encoder, E. This encoding is then used to sample, z∈$\mathbb{R}^k$, from the prior distribution, Q(z|X), assumed to be a multivariate Gaussian. Next z is concatenated with the conditional vector, c∈$\mathbb{R}^m$, and a reconstruction is generated using the decoder D([z, c]). During generation, the distribution $\mathcal{N}(0,1)$ is sampled for each varied component of z, the sample is concatenated with a given conditional c, and the decoder is sued to generate a new sample, D([z,c]).

The conditional variational autoencoder ("CVAE") model uses a convolutional decoder on mesh samples that share a topology at different hierarchical levels of coarsening, described above. Following FIG. 17, first a convolutional encoder, E, is used to compress input samples, $X \in \mathbb{R}^{N \times 3}$, down to a latent vector, $e = E(X) \in \mathbb{R}^{F_5}$ Next, e is mapped to a mean vector, $\mu \in \mathbb{R}^k$ and a standard deviation vector, $\sigma \in \mathbb{R}^k$, using two parallel fully-connected (FC) layers. These vector outputs are then used for variational inference during training with a reparameterization trick for variational autoencoders. Taking $e = E(X) \in \mathbb{R}^{F_5}$, where $e_i \in e$, each component of the latent vector can be varied as $z_i = \mu_i + \varepsilon \sigma_i \in \mathbb{R}^k$, where $\varepsilon \sim \mathcal{N}(0,1)$, therefore assuming a multivariate Gaussian distribution, $Q(z|X)$ that can be sampled from.

Next a random sample, z, can be concatenated with the associated conditional vector, c, to generate the mesh reconstruction, $\hat{X} = D([z,c])$. The spiral CVAE can be trained by minimizing the loss, $$\mathcal{L}_{gen} = \|X - \hat{X}\|_1 + w_{KL} KL(\mathcal{N}(0,I) \| Q(z|X))$$

with $w_{KL} = 0.001$, selected ad-hoc, acting as a weight on the KL divergence loss. The first term (reconstruction) minimizes the MAE between the reconstruction and ground truth sample, and the second term (KL divergence) acts as regularizer on the latent space by adding the constraint of a unit Gaussian prior with zero-mean on the latent space distribution, $Q(z|X)$.

Once trained, synthesizing new samples is straightforward. Since the KL divergence constrains the latent space to a unit Gaussian, new samples can be generated with the decoder by sampling an $\mathbb{R}^k$ vector from the unit Gaussian prior and concatenating it with a conditional prior vector, $c \in \mathbb{R}^m$, as a specification mechanism on the type of sample to be synthesized.

As described above, Grad-CAM can be adapted to provide an interpretable localized heatmap that weights the "importance" of areas in an image that are indicative of certain predictions after a model is trained. For example, class activation maps ("CAMs") can be extracted from a discriminative model to highlight areas, directly onto brain surfaces, that led to true positive ("TP") predictions in AD binary classification. This mesh adaptation of Grad-CAM can also be used to highlight the areas of the cortex and subcortical structures that are most indicative for predicting other diseases, conditions, or brain features, including fluid intelligence in children and adults.

As described above, using Grad-CAM, the gradients of the class scores (e.g., logits prior to softmax or sigmoid) with respect to the feature maps at the last convolutional layer (i.e., prior to GAP) are extracted. Using these gradients, GAP is applied on each feature map, per-class, to extract the "neuron importance weights," $\alpha_c^{(f)} \in \mathbb{R}^{c \times f}$, whose formulation can be readapted for meshes as described above, such that, $$\alpha_c^{(f)} = \frac{1}{N}\sum_i \frac{\partial y_c}{\partial A_i^{(f)}}$$

where $y_c$ again corresponds to the class score of class c, and $A_i^{(f)}$ refers to the value at vertex i in feature map $A^{(f)} \in \mathbb{R}^N$. The set of neuron importance weights, $\alpha_c^{(f)}$ is then projected back onto each feature map, $A^{(f)}$, to compute the CAMs, $M_c$ for each class, c, such that, $$M_c = ReLu\left(\sum_f \alpha_c^{(f)} A^{(f)}\right) \in \mathbb{R}^N$$

The ReLU is applied to the linear combination of maps because only the features that have a positive influence on the class of interest are considered relevant in this particular example.

As a consequence of multiple down-sampling operations within the discriminative network's architecture, extracted CAMs with respect to the number of vertices at the final convolutional layer are smoother and less focused to specific surface locations depending on the number of layers. Therefore, they can be up-sampled back to the same number of vertices as the input, using an interpolation, for a direct overlay onto the original input mesh.

In an example study, the discriminative and generative spiral networks were evaluated for several supervised and unsupervised tasks, respectively.

In this study, 8,665 T1-weighted 3D MRI volumes from the ADNI dataset, corresponding to 1,266 unique subjects, were used. For each scan, the healthy control ("HC"), mild cognitive impairment ("MCI"), or Alzheimer's disease ("AD") labels were given up to 2 months after the corresponding scan in ADNI. This was done as a precaution to ensure that each diagnosis had clinical justification. The dataset included 2,758/3,959/1,948 samples for the HC/MCI/AD labels, respectively.

Each discriminative model in this study was designed to classify pathological (AD/MCI) scans apart from HCs. To ensure that scans from the same subject did not appear in different sets, all data splits (train/test/validation) in this study shuffled samples by subject identifiers instead of scan identifiers. The data were randomly split into training/testing sets (85%, 15%) across subjects, and a 5-fold cross-validation across the subjects was used within the training set in the subsequent analyses.

Meshes were extracted from each T1-weighted MRI sample using the mesh extraction preprocessing methods described above. Each subcortical region was represented using an independent surface mesh with the corresponding number of vertices, per hemisphere. A mesh object for one hemisphere of a subcortical region can be represented using a vertex feature matrix, $X \in \mathbb{R}^{N \times 3}$, described above, and a corresponding set of faces, $\mathcal{F}$, which is a set of 3-element tuples where each tuple indexing the vertices that make up the corresponding triangular face on the mesh.

The vertex feature matrix of a mesh sample containing a single bilateral subcortical region (i.e., LH/RH hippocampi) was constructed using a row-wise concatenation (vertical stacking) of the vertex feature matrix for each hemisphere of the corresponding subcortical region. The sets of faces for each hemisphere of the same subcortical region were merged to create one set faces for the bilateral subcortical region sample type. For mesh samples representing a single hemisphere or all subcortical regions, the corresponding vertex feature matrix and set of faces was obtained using the same vertical stacking and merging process. Each mesh sample type can be interpreted as an undirected graph described by a vertex feature matrix, X, and the corresponding set of faces, $\mathcal{F}$. Therefore, 14,848 vertices were used to represent a single mesh sample for all subcortical regions, 7,424 vertices for a single hemisphere, and 2N vertices per subcortical region, for each corresponding N.

Following the encoder module described above and depicted in FIG. 14, the topology of spiral sequences at each level of mesh coarsening is only preprocessed once. In-order, the spiral lengths, $\ell_r$, used for the spiral filters within the r-th ResBlock of the encoder are $\{\ell_r\}_{r=1}^5 = \{12,12,12,12,9\}$ with the corresponding dilation parameters, $\{d_r\}_{r=1}^5 = \{2,2,2,1,1\}$. These parameters are used in reverse-order for the ResBlocks within the convolutional decoder, depicted in FIG. 15. Following the steps described above, down/up-sampling matrices are generated once to represent surfaces in this study at multiple hierarchical levels while still preserving context at each level. Again following the structure of the encoder (FIG. 14), meshes are specifically up/down-sampled within the architecture by a factor of 2 for each mesh sampling operation. At each level of coarsening, spiral sequences are generated once using the template mesh.

Discriminative models and hyperparameter tuning were evaluated using the 5-fold cross-validation on the training set, as described above, for two separate experiments. An experiment was conducted with the discriminative model to analyze the efficacy of incorporating input data from multiple subcortical structures for binary AD/MCI classification, in comparison to input data from a single hemisphere or single structure. The number of filters, per convolutional layer, at the rth ResBlock, within the encoder was $\{F_r\}_{r=1}^5 = \{32,64,64,128,128\}$. A binary cross-entropy ("BCE") objective function was used to train all discriminative models using the AdamW optimizer with a learning rate of $2 \times 10^{-4}$ learning rate decay of 0.99 for every step, and a batch size of 16 samples per batch over 200 epochs. In addition to the BCE loss, the weights of the network were also L2-regularized with a weight decay of $1 \times 10^{-5}$.

Binary classification tasks were performed on different combinations of subcortical structures to classify scans using the diagnostic labels provided by ADNI. The first task was to classify HC scans apart from those belonging to subjects with AD, meanwhile the second task looked at HC versus MCI classification. For each task, the same discriminative spiral network (architecture and number of parameters) described above was used, and each model was trained on the same task, each with a varied combination of input structures. Classifiers were trained and compared with single-structure (both hemispheres), single hemisphere, and all-structure mesh inputs for each sample.

Results for in-vivo AD versus HC classification with spiral networks on brain surface meshes demonstrated the powerful discriminative advantage in learning surface representations of subcortical brain structures. Spiral CNNs can outperform recent methods that operate on point cloud representations or use spectral graph convolution on the same template-registered meshes in this study.

The CAMs obtained using the discriminative model draw direct correspondences with the literature regarding localized areas of deformation related to AD pathology. Paired with the discriminative model, the framework described in the present disclosure combines localized contextual visualization together with classification results. Advantageously, the techniques described in the present disclosure provide a modular visualization method that provides context to a discriminative model's predictions without making architectural changes to the model, which is highly desirable for establishing appropriate trust in predictive models.

Furthermore, the results of the generative model demonstrate the potential for using diagnosis in the condition vector as a means to add more specificity to the type of output that is generated. The generative framework illustrates a potential application for generating synthetic training data that would be beneficial for improving deep learning frameworks that benefit from increased dataset sizes. Significant volume and surface area changes with respect to AD diagnosis were identified, particularly in the amygdala, caudate, nucleus accumbens, right putamen, thalamus, and most importantly the hippocampus, an area of the brain highly correlated with AD.

Thus, the systems and methods of the described embodiments enable to classification of disease, conditions, or brain features based on brain shape using discriminative and generative networks that learn and operate directly on surface meshes by way of geometric deep learning. The framework is constructed by a variety of modular computational blocks that are used by both the discriminative and generative models. Notably, the convolutional encoder learns effective shape descriptors that can be used for AD (or other disease or condition) classification by the discriminative model. The first analysis demonstrates an improvement in AD classification performance using the same model with varying input types: single subcortical region, subcortical regions within a single hemisphere, and bilateral subcortical regions. The results of the aforementioned example study demonstrate an advantage to the joint modeling of multiple subcortical structures for in-vivo AD classification.

Additionally, the generative model's decoder module is able to reconstruct 3D mesh inputs from their low-dimensional shape descriptors obtained by the encoder. In using a variational approach, a probabilistic latent space can be learned, which can be sampled from to generate synthetic samples for each subcortical structure with respect to phenotype information, in particular: AD diagnosis. The endemic nature of medical imaging data, particularly within neuroimaging, attributes to scarcity of open-access neuroimaging databases. The generative model is able to generate realistic-looking synthetic examples, which may be used to train other deep learning approaches that often require large datasets and annotated data is limited.

The proposed discriminative network can be further tailored to fuse other phenotypic data for AD classification; including but not limited to: chronological age, sex assignment at birth, genotype data, etc. Phenotype features can also be used as additional conditional priors in the generative framework, adding additional constraints for synthesizing personalized samples.

Natural extensions can include expanding the classification task to sub-typing different stages of mild cognitive impairment (e.g., early versus late), using spiral convolution within a recurrent neural network framework for longitudinal predictions related to AD, generating template-registered 3D meshes from MRI volume inputs using a spiral convolutional decoder framework to automate the mesh extraction preprocessing steps, and the like.

In yet another example, the systems and methods described in the present disclosure can be implemented to predict or otherwise characterize a condition of a subject's brain, such as a prediction or probability of whether the subject has or will develop a disease (e.g., Alzheimer's disease dementia) or another neurological condition. In this example, a graph convolutional network is implemented to estimate a fluid intelligence of a subject, as described below in more detail.

Fluid intelligence refers to the ability to solve novel reasoning problems, which is considered independent of experience and education and, as such, believed to be biologically grounded on neurodevelopment. Previous studies have reported an age-related performance in fluid intelligence ("Gf"), peaking in late adolescence and declining in adulthood.

In this example study, two datasets of subjects at distinct phases of cognitive maturation were evaluated. The younger cohort, the ABCD dataset, included children from 9 to 11 years, an age at which fluid intelligence has not yet reached its putative maximum. In this cohort, Gf was predicted with R=0.328. More studies have attempted to predict fluid intelligence using the HCP dataset. The age of subjects in the HCP dataset ranges from 22 to 35 years old, which corresponds to a different maturational phase when fluid intelligence is close to its full potential. Previous studies predicting fluid intelligence in the HCP dataset have done so using functional MRI ("fMRI"). The systems and methods described in the present disclosure are capable of achieving an R=0.454 for estimating fluid intelligence, using T1-weighted anatomic MRI data without any behavioral or functional imaging data. These results support an association between brain morphometry and Gf. Moreover, this association can be strengthened when both cortical and subcortical structure shapes informed the gCNNs.

In this example study, brain surface data (e.g., cortical surface data, subcortical surface data) were generated from magnetic resonance images similar to the embodiments described above. Surface templates were converted to graphs based on their triangulation scheme. Nodes of the graphs were surface vertices, and edges of the graphs were segments across vertices. Overall, the graphs including all structures had 47,616 nodes, 32,768 from the cortical surfaces and 14,848 from the subcortical surfaces. Input features of the network were defined as the Cartesian coordinates of surface vertices in subjects' native space resampled into the surface templates. As a consequence, cortical nodes were assigned 6 features (X, Y, Z of both the inner and outer cortical surface vertices) and subcortical nodes had 3 features (X, Y, Z of subcortical surface vertices) when they were used for separate training.

Nested cross-validation was used in this example study to assess generalizability, which contains an outer loop of six folds and an inner loop of five folds. Both datasets were split into six folds, randomly selecting one set as the outer test set and the rest five sets as the outer training set. This whole process repeats six times for each fold. The outer training set was sub-divided into five folds, including one validation set and four inner training sets. This inner process repeated five times and the outer test set was evaluated by an ensembled model averaged from those five trained models.

Traditional CNNs extract features on structured data, such as 2D images or 3D volumes. The convolution operations over graphs can be generalized in the spectral domain, which is the multiplication of the signal on graphs with the eigenvector matrix of the graph Laplacian. An undirected graph, G, can be defined as described above.

In order to increase the generalizability between two datasets, data augmentation techniques can be used, including random rotation within ±20 degrees and a random Gaussian noise standardized with mean $\mu=0$ and a standard deviation of $\sigma=0.02$. The augmentation parameter, $p_a$, denotes the probability of the use of data augmentation for a single subject. In this study, both datasets had $p_a=0.5$, indicating that data augmentation was applied with a 50% probability per subject for each iteration of training.

Figure 18:
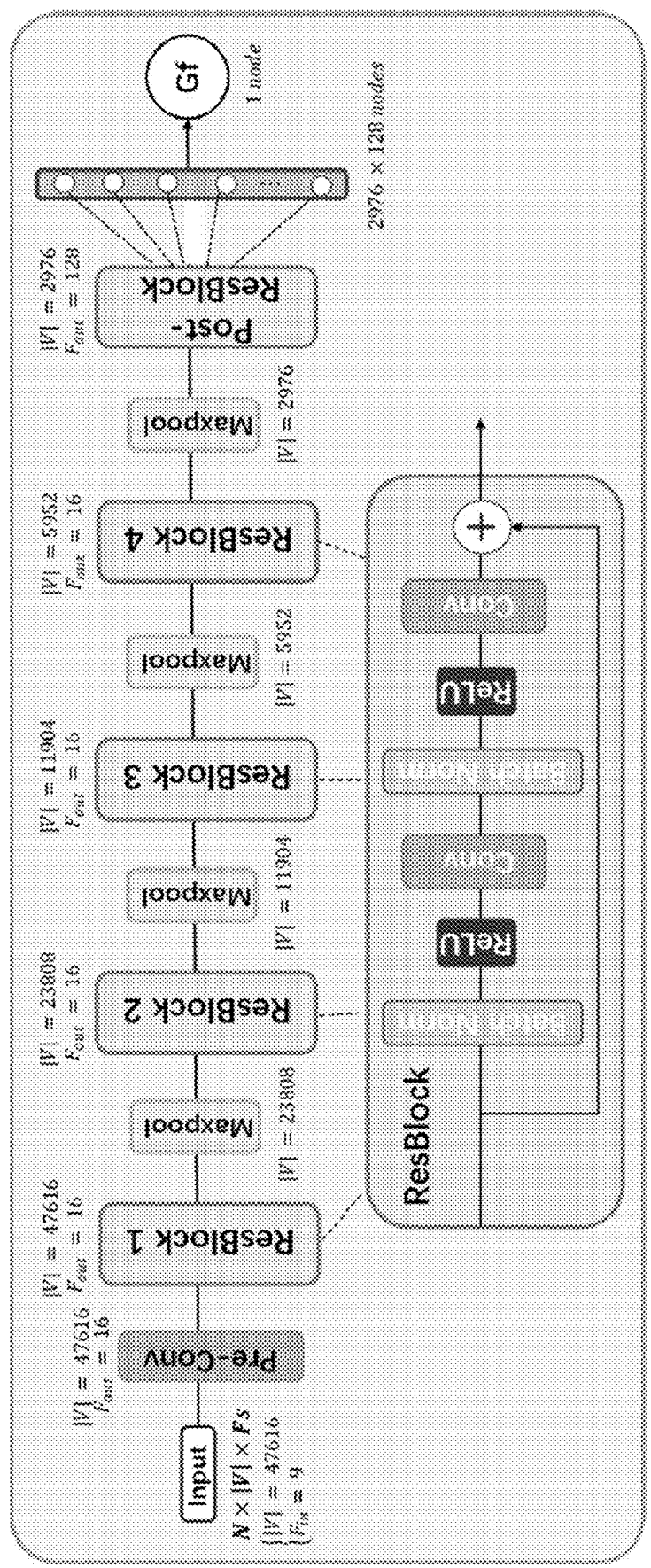
FIG. 18 is an example model architecture that may be implemented to estimate a fluid intelligence score from brain surface morphology. The model contains a pre-convolutional layer, four residual blocks, and a post residual block, followed by a fully connected layer. Each residual block has two subblocks, each with a batch normalization layer, a ReLU, and a convolutional layer. Each residual block is followed by a max pooling layer to downsample the features. N is the number of batch size; |Vi is the number of vertices; F is the number of features.
Figures 19A, 19B, 19C, 19D:
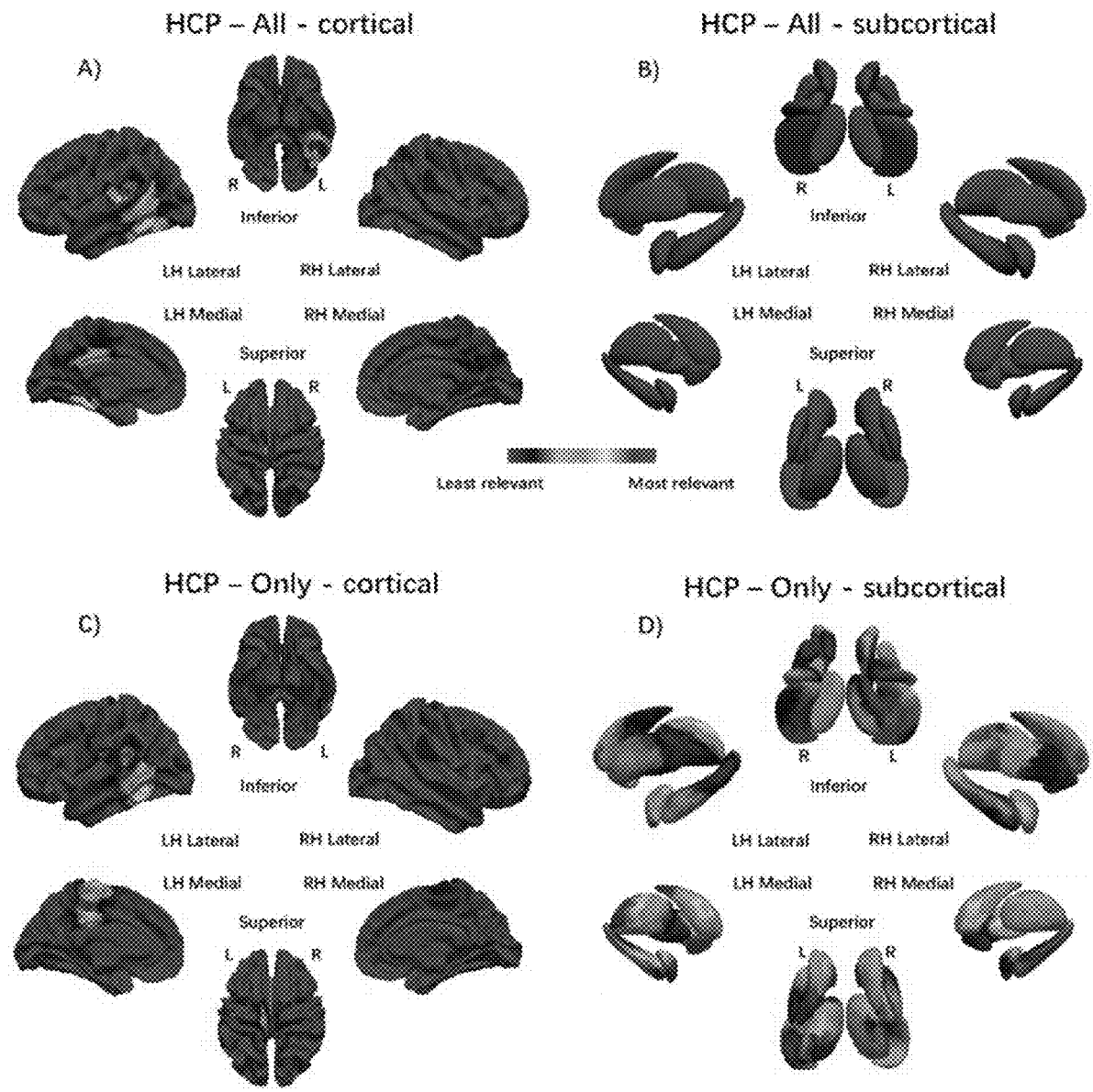
FIGS. 19A-19D show Grad-CAM visualizations on the HCP dataset using both cortical and subcortical structures as input. Brain regions predictive of fluid intelligence are indicated in the CAMs. The red regions corresponds to regions that were more informative for the score prediction.
Figures 20A, 20B, 20C, 20D:
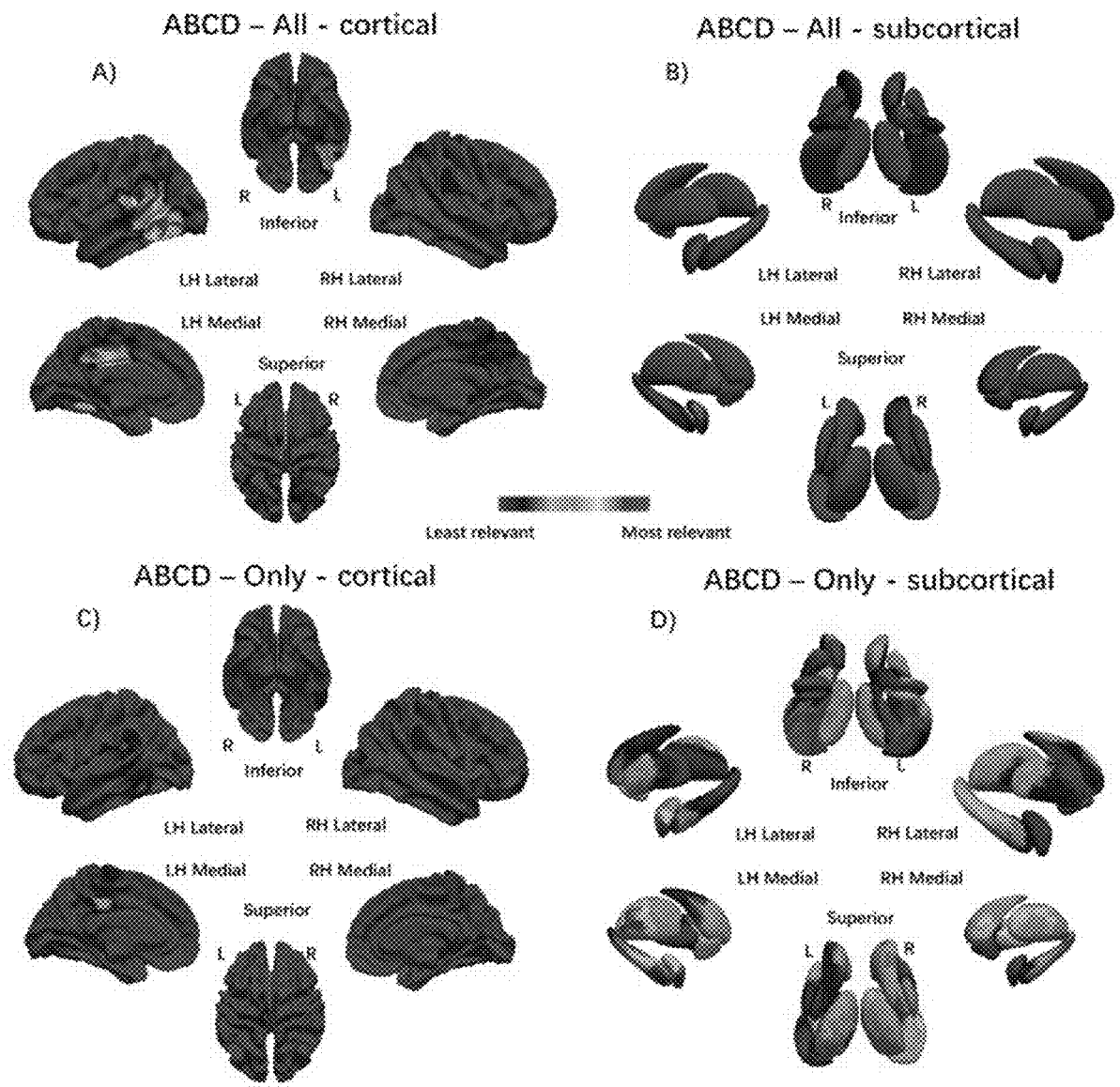
FIGS. 20A-20D show Grad-CAM visualizations on the ABCD dataset using both cortical and subcortical structures as input. Brain regions predictive of fluid intelligence are indicated in the CAMs. The red regions corresponds to regions that were more informative for the score prediction.

FIG. 18 shows the details of an example graph network. Residual blocks are used in the example model to facilitate the training of deeper networks. Using this approach, the output of the previous block is added to the output of the current block to avoid the vanishing gradient problem. The model contains a pre-convolutional layer (Pre-Conv), four residual blocks (ResBlock) and a post residual block, followed by a single fully connected (FC) layer with one output that reflects the estimated fluid intelligence (Gf) score. Each residual block has two subblocks, including a batch normalization layer (BN), a non-linear activation function ReLU and a normal convolutional layer (Conv). The maxpooling layer is used after each residual block to downsample the features.

The loss function used in the model in this example is composed of three parts: the mean square error ("MSE") between the network's estimations and actual values, the Pearson's coefficient of correlation (corr), and an additional l2 regularization term. The loss, $L_{all}$, can be defined as, $$L_{all} = MSE + \lambda_1 \cdot l_2 - \lambda_2 \cdot \text{corr}$$

for, $$\text{corr} = \frac{\text{cov}(y^p, y^t)}{\sigma_{y^p} \cdot \sigma_{y^t}}$$

where $\lambda_1$ and $\lambda_2$ are the regularization parameters, $y^p$ is the predicted score, $y^t$ is the true label, cov is the covariance, and $\sigma$ is the standard deviation. This correlation term is added to alleviate regression towards the mean ("RTM") bias, where the higher the correlation, the lower the loss.

As with the other embodiments described above, to visualize the most relevant brain areas involved in the network's decision making process and to provide some interpretability to the network results, a Grad-CAM method can be applied to generate a color-coded probability map, $M_c$. Grad-CAM uses the gradient information flowing back to the last convolutional layer of the model to generate heatmaps highlighting important regions upon which the model focuses and then performs a global average pooling operation to produce the importance weights, $\alpha_c^k$ of each neuron, as described above.

After getting the weights, $M_c$ is calculated with a weighted combination of feature maps followed by an activation function (e.g., ReLU), which is applied to only take positive weights into consideration and ignore the negative weights since the features-of-interest are those with positive influence on the class of interest.

Grad-CAM maps were obtained for Gf (i.e., fluid intelligence) prediction from each testing set in all six folds. In some model implementations, four pooling layers are used, thereby reducing the number of nodes by a factor 24. In these instances, the generated Grad-CAM maps can be rescaled back to the original size using spherical linear interpolation on the cortical and subcortical surfaces in order to overlay on the original graphs.

Model performance was evaluated using nested cross-validation, with the datasets split into six folds each, where each fold was randomly chosen for testing and the remaining five folds were used for training. In each fold, the outer test dataset was evaluated by an averaged model ensembled from all five inner-folds models, and the Grad-CAMs were generated using the average weighted sum on each of the testing subject.

For the ABCD dataset, the networks were trained using a batch size of 32, and a maximum number of epochs of 100. Adam optimizer with a learning rate of 0.0005 and a decay rate of 0.99 per ten steps was used, the parameters $\lambda_1$ and $\lambda_2$ were both set to 0.0001 and the dropout ratio at the fully connected layer was set to 0.5. For the HCP dataset, the batch size was set to 50 and the parameter $\lambda_1$ was set to 0.0005. Due to the smaller dataset size, the maximum number of epochs for the HCP dataset was set to 80. The different network parameters were optimized using cross-validation and the training process stopped when the generalization error increased with the patience factor set to five.

The example study had three aims: to identify the most predictive brain morphometric features of Gf (i.e., fluid intelligence), to assess the contribution of the subcortical morphometry to Gf either alone or combined with cortical morphology, and to investigate how age might be involved in the prediction of Gf. The residual gCNNs described in the present disclosure were used to infer Gf from cortical and subcortical surface models that integrated multiple morphometric features, such as cortical thickness, cortical area, and gyrification, as well the shape of subcortical structures.

Using two large and independent datasets of pre-adolescent (ABCD project) and young adults (HCP dataset) and a nested six-fold cross-validation scheme, this analysis predicted Gf with significant correlations (R=0.31-0.45). Across both datasets, the right amygdala and hippocampus, left temporal and parietal cortex, and bilateral cingulate morphometry consistently drove the prediction of Gf Given the uniqueness of these findings, particularly for the amygdala and temporal cortex, localization was confirmed using Grad-CAM to show reproducibility across subcortical surfaces and gyral folds. Example CAM maps for the HCP data are shows in FIGS. 19A-19D, and for the ABCD data set in FIGS. 20A-20D.

Divergence between the datasets was observed whereby the left hippocampus and amygdala, right caudate, right nucleus accumbens (NAc) and right pallidum also helped predict Gf for the younger ABCD cohort, with subcortical structures alone producing an R~0.27, and cortical structures alone producing an R~0.3. Together, subcortical and cortical structures produced an R~0.31 for the younger ABCD cohort, whereas for the older HCP cohort, the combined was higher (R~0.45). For the older HCP cohort, furthermore, subcortical structures alone producing an R~0.1, and cortical structures alone produced an R~0.4, with the right rectus gyrus helping predict Gf for the older HCP cohort but not the ABCD cohort.

In both datasets, significantly better predictions were thus obtained by combining the cortical and subcortical surfaces. Despite this commonality regarding improved Gf prediction through combining cortical and subcortical morphometric features, the younger ABCD cohort had a substantially larger contribution from medial temporal and basal ganglia brain regions than the older HCP cohort, which can be considered in the context of differences in the trajectory of brain development between the late latency/pre-adolescence (ABCD cohort) and late adolescence/young adulthood (HCP cohort).

In some embodiments, the systems and methods described in the present disclosure can estimate brain age in whole brain radiotherapy patients, thereby characterizing neurocognitive toxicity. The surface-based deep learning ("SBDL") techniques described in the present disclosure implement deep learning using convolutional neural network architectures applied to surface meshes of the brain's geometric surfaces. This method provides an unbiased, data-driven approach to determine an individual subject's "brain age" using T1-weighted brain MRI data. The application of geometric deep learning to image-based applications is successful in the accurate prediction of brain age. It is contemplated that the prediction of brain age can serve as a surrogate marker for neurocognitive functioning following brain radiotherapy given the similarities between cognitive deterioration in aging and cognitive decline following brain radiotherapy, specifically as it relates to the cognitive domains of memory, processing speed, and executive function.

Thus, in some embodiments, SBDL techniques are used to characterize changes in brain age that follow the completion of standard whole brain radiotherapy. For example, the method 100 shown in FIG. 1 can be performed to generate brain feature data that indicate a brain age for a subject following whole brain radiotherapy. By comparing this estimated brain age to a pre-treatment brain age value, the changes in brain age resulting from the whole brain radiotherapy can be evaluated. SBDL-based brain age prediction following completion of standard whole brain radiotherapy can demonstrate alterations in brain shape following completion of standard whole brain radiotherapy for the treatment of brain metastases.

In some other embodiments, electrophysiologically abnormal brain regions can be identified using the systems and methods described in the present disclosure. Given limited available patient data in epilepsy, an autoencoder permitting single-subject analysis can be implemented. Graph convolutional network-based analysis via a surface-based deep auto encoder ("SBDAE") using T1-weighted MRI data can provide valuable insights for use in epilepsy care.

For example, SBDAE can accurately identify electrophysiologically ("EP") abnormal brain regions as determined by iEEG analysis. Patients who have previously undergone iEEG investigation can be analyzed individually to determine the predictive power of SBDAE to localize EP abnormal brain regions defined by previous iEEG analysis. EP abnormal brain regions (including locations of seizure onset and propagation) can be mapped in MRI space. Single subject results can be compared to determine the degree of overlap between the mapped iEEG-defined EP findings and SBDAE-mapped morphologic brain anomalies. It is contemplated that these technique can determine abnormal brain regions in patients with cryptogenic epilepsy and/or to predict the likelihood for seizure freedom in patients who underwent resection for refractory epilepsy.

Additionally or alternatively, a graph-based variational autoencoder ("gVAE") can be used to learn the patterns of resting state functional MRI (rsfMRI) within the brain's subcortical structures in healthy subjects and reconstruct it in patients with epilepsy to identify findings unique to patients with epilepsy. The graph variational autoencoder network can also be enriched with long short-term memory ("LSTM") and perceptual loss to learn temporal resting-state fMRI features and to smooth the reconstructed signals.

In still other embodiments, the systems and methods described in the present disclosure can be used to evaluate accelerated brain aging in patients affected by various diseases or conditions. For example, it is contemplated that HIV infections can result in accelerated brain aging, leading to potential cognitive decline.

Figure 21:
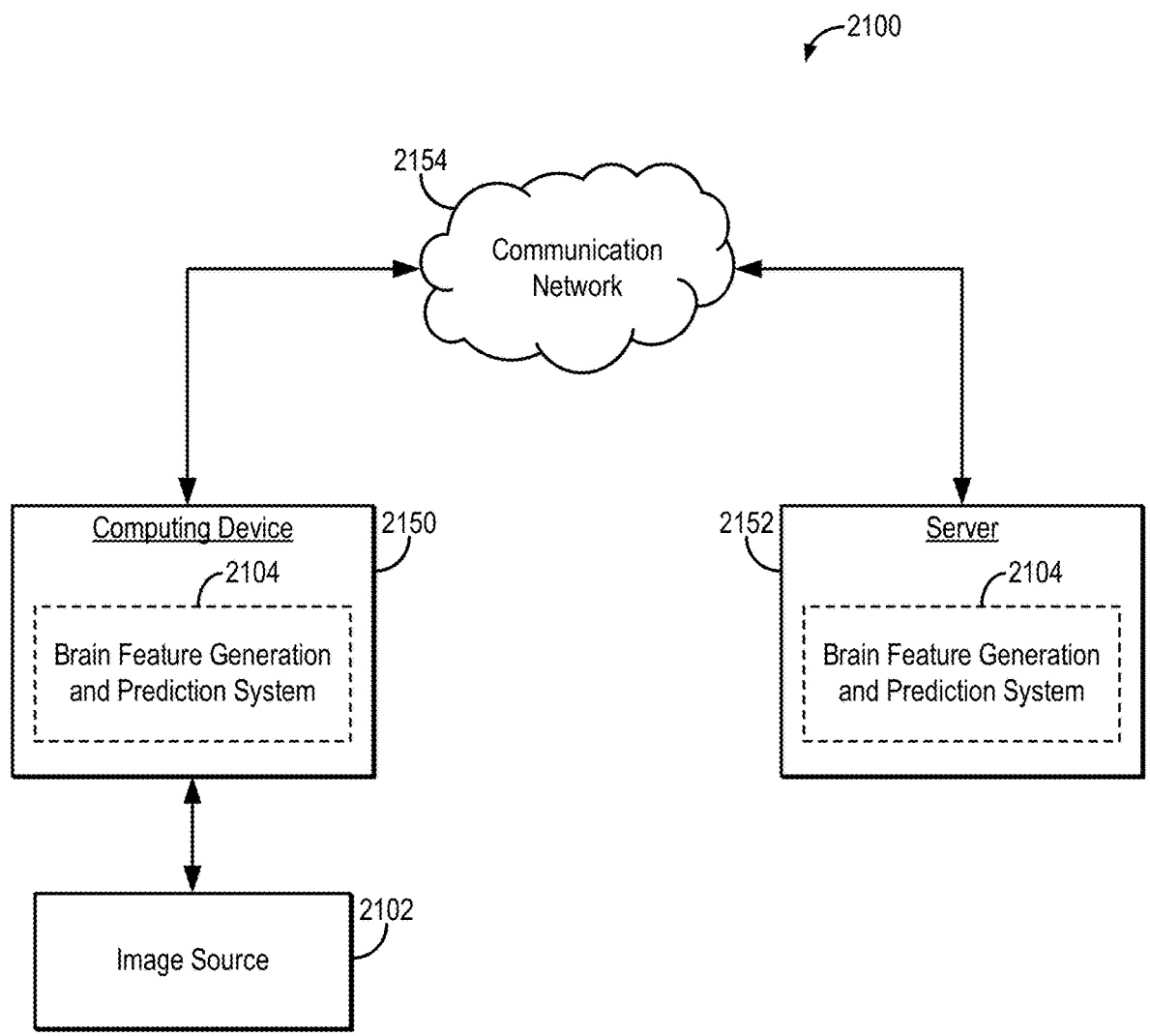
FIG. 21 is a block diagram of an example brain feature data generation and prediction system.

Referring now to FIG. 21, an example of a system 2100 for generating brain feature data in accordance with some embodiments of the systems and methods described in the present disclosure is shown. As shown in FIG. 21, a computing device 2150 can receive one or more types of data (e.g., image data) from image source 2102, which may be a magnetic resonance image source. In some embodiments, computing device 2150 can execute at least a portion of a brain feature generation and prediction system 2104 to generate and/or classify brain feature data from image data received from the image source 2102.

Additionally or alternatively, in some embodiments, the computing device 2150 can communicate information about data received from the image source 2102 to a server 2152 over a communication network 2154, which can execute at least a portion of the brain feature generation and prediction system 2104. In such embodiments, the server 2152 can return information to the computing device 2150 (and/or any other suitable computing device) indicative of an output of the brain feature generation and prediction system 2104.

In some embodiments, computing device 2150 and/or server 2152 can be any suitable computing device or combination of devices, such as a desktop computer, a laptop computer, a smartphone, a tablet computer, a wearable computer, a server computer, a virtual machine being executed by a physical computing device, and so on. The computing device 2150 and/or server 2152 can also reconstruct images from the data.

In some embodiments, image source 2102 can be any suitable source of image data (e.g., measurement data, images reconstructed from measurement data), such as an MRI system, another computing device (e.g., a server storing image data), and so on. In some embodiments, image source 2102 can be local to computing device 2150. For example, image source 2102 can be incorporated with computing device 2150 (e.g., computing device 2150 can be configured as part of a device for capturing, scanning, and/or storing images). As another example, image source 2102 can be connected to computing device 2150 by a cable, a direct wireless link, and so on. Additionally or alternatively, in some embodiments, image source 2102 can be located locally and/or remotely from computing device 2150, and can communicate data to computing device 2150 (and/or server 2152) via a communication network (e.g., communication network 2154).

In some embodiments, communication network 2154 can be any suitable communication network or combination of communication networks. For example, communication network 2154 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 2154 can be a local area network, a wide area network, a public network (e.g., the Internet), a private or semi-private network (e.g., a corporate or university intranet), any other suitable type of network, or any suitable combination of networks. Communications links shown in FIG. 21 can each be any suitable communications link or combination of communications links, such as wired links, fiber optic links, Wi-Fi links, Bluetooth links, cellular links, and so on.

Figure 22:
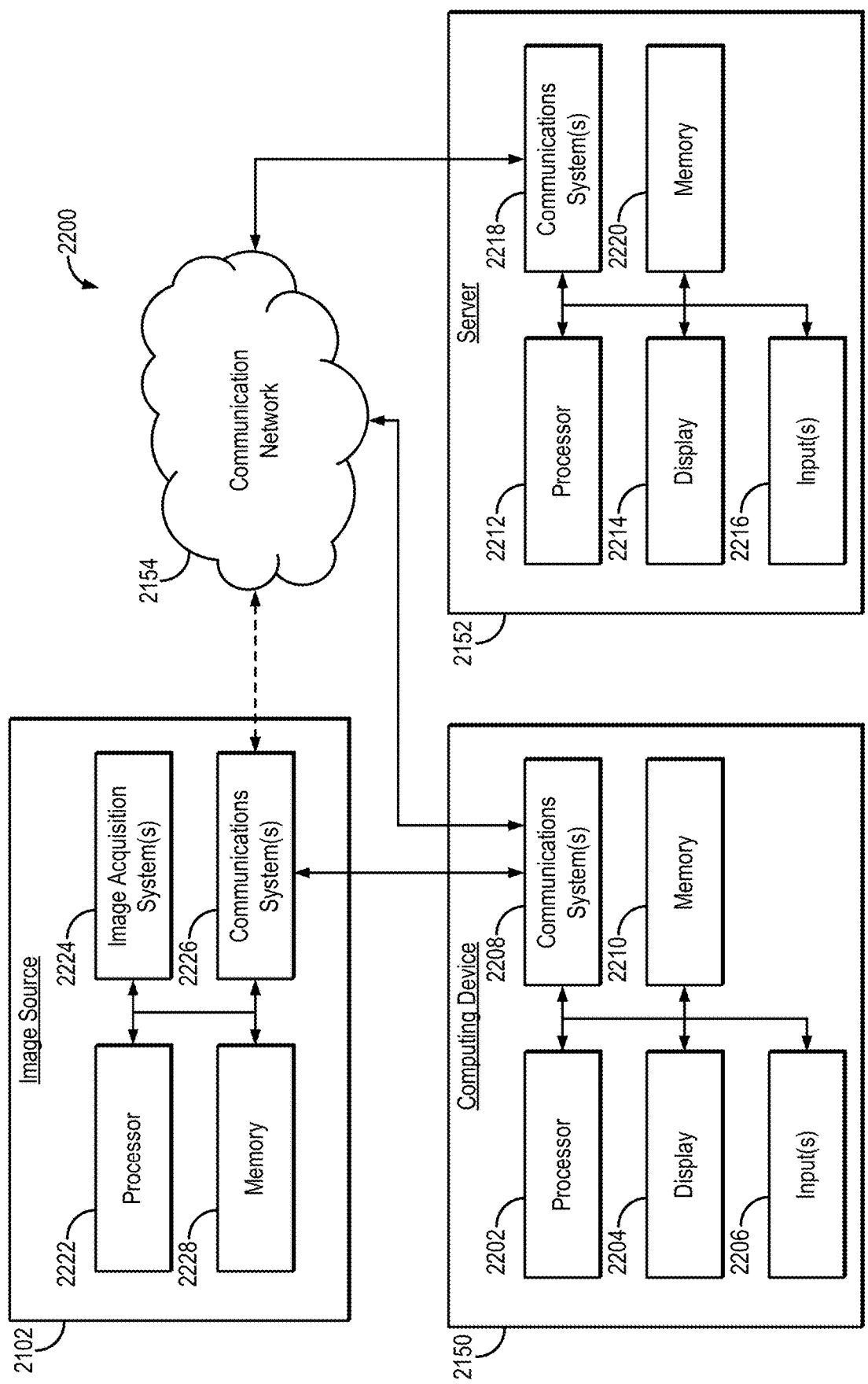
FIG. 22 is a block diagram of example components that can implement the brain feature data generation and prediction system of FIG. 21.

Referring now to FIG. 22, an example of hardware 2200 that can be used to implement image source 2102, computing device 2150, and server 2152 in accordance with some embodiments of the systems and methods described in the present disclosure is shown. As shown in FIG. 22, in some embodiments, computing device 2150 can include a processor 2202, a display 2204, one or more inputs 2206, one or more communication systems 2208, and/or memory 2210. In some embodiments, processor 2202 can be any suitable hardware processor or combination of processors, such as a central processing unit ("CPU"), a graphics processing unit ("GPU"), and so on. In some embodiments, display 2204 can include any suitable display devices, such as a computer monitor, a touchscreen, a television, and so on. In some embodiments, inputs 2206 can include any suitable input devices and/or sensors that can be used to receive user input, such as a keyboard, a mouse, a touchscreen, a microphone, and so on.

In some embodiments, communications systems 2208 can include any suitable hardware, firmware, and/or software for communicating information over communication network 2154 and/or any other suitable communication networks. For example, communications systems 2208 can include one or more transceivers, one or more communication chips and/or chip sets, and so on. In a more particular example, communications systems 2208 can include hardware, firmware and/or software that can be used to establish a Wi-Fi connection, a Bluetooth connection, a cellular connection, an Ethernet connection, and so on.

In some embodiments, memory 2210 can include any suitable storage device or devices that can be used to store instructions, values, data, or the like, that can be used, for example, by processor 2202 to present content using display 2204, to communicate with server 2152 via communications system(s) 2208, and so on. Memory 2210 can include any suitable volatile memory, non-volatile memory, storage, or any suitable combination thereof. For example, memory 2210 can include RAM, ROM, EEPROM, one or more flash drives, one or more hard disks, one or more solid state drives, one or more optical drives, and so on. In some embodiments, memory 2210 can have encoded thereon, or otherwise stored therein, a computer program for controlling operation of computing device 2150. In such embodiments, processor 2202 can execute at least a portion of the computer program to present content (e.g., images, user interfaces, graphics, tables), receive content from server 2152, transmit information to server 2152, and so on.

In some embodiments, server 2152 can include a processor 2212, a display 2214, one or more inputs 2216, one or more communications systems 2218, and/or memory 2220. In some embodiments, processor 2212 can be any suitable hardware processor or combination of processors, such as a CPU, a GPU, and so on. In some embodiments, display 2214 can include any suitable display devices, such as a computer monitor, a touchscreen, a television, and so on. In some embodiments, inputs 2216 can include any suitable input devices and/or sensors that can be used to receive user input, such as a keyboard, a mouse, a touchscreen, a microphone, and so on.

In some embodiments, communications systems 2218 can include any suitable hardware, firmware, and/or software for communicating information over communication network 2154 and/or any other suitable communication networks. For example, communications systems 2218 can include one or more transceivers, one or more communication chips and/or chip sets, and so on. In a more particular example, communications systems 2218 can include hardware, firmware and/or software that can be used to establish a Wi-Fi connection, a Bluetooth connection, a cellular connection, an Ethernet connection, and so on.

In some embodiments, memory 2220 can include any suitable storage device or devices that can be used to store instructions, values, data, or the like, that can be used, for example, by processor 2212 to present content using display 2214, to communicate with one or more computing devices 2150, and so on. Memory 2220 can include any suitable volatile memory, non-volatile memory, storage, or any suitable combination thereof. For example, memory 2220 can include RAM, ROM, EEPROM, one or more flash drives, one or more hard disks, one or more solid state drives, one or more optical drives, and so on. In some embodiments, memory 2220 can have encoded thereon a server program for controlling operation of server 2152. In such embodiments, processor 2212 can execute at least a portion of the server program to transmit information and/or content (e.g., data, images, a user interface) to one or more computing devices 2150, receive information and/or content from one or more computing devices 2150, receive instructions from one or more devices (e.g., a personal computer, a laptop computer, a tablet computer, a smartphone), and so on.

In some embodiments, image source 2102 can include a processor 2222, one or more image acquisition systems 2224, one or more communications systems 2226, and/or memory 2228. In some embodiments, processor 2222 can be any suitable hardware processor or combination of processors, such as a CPU, a GPU, and so on. In some embodiments, the one or more image acquisition systems 2224 are generally configured to acquire data, images, or both, and can include an MRI system. Additionally or alternatively, in some embodiments, one or more image acquisition systems 2224 can include any suitable hardware, firmware, and/or software for coupling to and/or controlling operations of an MRI system. In some embodiments, one or more portions of the one or more image acquisition systems 2224 can be removable and/or replaceable.

Note that, although not shown, image source 2102 can include any suitable inputs and/or outputs. For example, image source 2102 can include input devices and/or sensors that can be used to receive user input, such as a keyboard, a mouse, a touchscreen, a microphone, a trackpad, a trackball, and so on. As another example, image source 2102 can include any suitable display devices, such as a computer monitor, a touchscreen, a television, etc., one or more speakers, and so on.

In some embodiments, communications systems 2226 can include any suitable hardware, firmware, and/or software for communicating information to computing device 2150 (and, in some embodiments, over communication network 2154 and/or any other suitable communication networks). For example, communications systems 2226 can include one or more transceivers, one or more communication chips and/or chip sets, and so on. In a more particular example, communications systems 2226 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 2228 can include any suitable storage device or devices that can be used to store instructions, values, data, or the like, that can be used, for example, by processor 2222 to control the one or more image acquisition systems 2224, and/or receive data from the one or more image acquisition systems 2224; to images from data; present content (e.g., images, a user interface) using a display; communicate with one or more computing devices 2150; and so on. Memory 2228 can include any suitable volatile memory, non-volatile memory, storage, or any suitable combination thereof. For example, memory 2228 can include RAM, ROM, EEPROM, one or more flash drives, one or more hard disks, one or more solid state drives, one or more optical drives, and so on. In some embodiments, memory 2228 can have encoded thereon, or otherwise stored therein, a program for controlling operation of image source 2102. In such embodiments, processor 2222 can execute at least a portion of the program to generate images, transmit information and/or content (e.g., data, images) to one or more computing devices 2150, receive information and/or content from one or more computing devices 2150, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), Flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for generating brain feature data from medical images, the method comprising:
   (a) accessing medical image data with a computer system, wherein the medical image data comprise medical images that depict a brain of a subject;
   (b) accessing a neural network with the computer system, wherein the neural network is trained to take input as brain surface data and generate output as brain feature data;
   (c) generating brain surface data from the medical image data using the computer system, wherein the brain surface data represent at least one of a cortical surface or a subcortical surface of the subject's brain;
   (d) generating graph representation data of the brain surface data using the computer system, wherein the graph representation data represent a brain surface as a graph of connected nodes;
   (e) inputting the graph representation data to the neural network, generating output as brain feature data that indicate at least one brain feature of the subject's brain; and
   (f) outputting the brain feature data to a user.

2. The method of claim 1, wherein the neural network is a graph convolutional neural network.

3. The method of claim 2, wherein the graph convolutional neural network is a spectral graph convolutional neural network.

4. The method of claim 1, wherein the neural network is a graph-based autoencoder network.

5. The method of claim 4, wherein the graph-based autoencoder network comprises a discriminative network including a convolutional encoder module and a multilayer perceptron.

6. The method of claim 5, wherein the graph representation data comprise a three-dimensional mesh graph representation.

7. The method of claim 5, wherein the convolutional encoder module includes spiral residual blocks and the graph representation data include spiral sequences determined from the graph of connected nodes.

8. The method of claim 1, wherein the brain surface data comprise at least one of an inner cortical surface of the subject's brain, an outer cortical surface of the subject's brain, or a subcortical surface of the subject's brain.

9. The method of claim 8, wherein the brain surface data comprise both an inner cortical surface and an outer cortical surface of the subject's brain.

10. The method of claim 8, wherein the brain surface data comprise an inner cortical surface, an outer cortical surface, and at least one subcortical surface of the subject's brain.

11. The method of claim 1, further comprising generating a class activation map using the computer system and the brain feature data, wherein the class activation map provides a visual depiction of regions of the subject's brain that influenced generation of the brain feature data using the neural network.

12. The method of claim 11, wherein the class activation map is generated by:
    extracting gradients for each class score at a last convolutional layer of the neural network;
    computing neuron importance weights using a global average pooling operation for each brain feature per class; and
    generating the class activation map by weighting brain feature maps using associated neuron importance weights.

13. The method of claim 11, wherein outputting the brain feature data to the user includes overlaying the class activation map on the brain surface data.

14. The method of claim 1, wherein the brain feature data indicate a classification of the subject's brain as being indicative of Alzheimer's disease.

15. The method of claim 1, wherein the brain feature data indicate a classification of the subject's brain as being indicative of mild cognitive impairment.

16. The method of claim 1, wherein the brain feature data comprise an estimate of a brain age of the subject's brain.

17. The method of claim 16, wherein the brain feature data comprise an estimate of the brain age of the subject's brain as accelerated by a disease.

18. The method of claim 16, wherein the brain feature data comprise an estimate of the brain age of the subject's brain as accelerated by radiotherapy administered to the subject's brain.

19. The method of claim 1, wherein the brain feature data comprise an estimate of a fluid intelligence score for the subject.

20. The method of claim 1, wherein the brain surface data comprise a mesh surface and generating the graph representation data comprises converting the mesh surface to a graph representation of the mesh surface.

21. The method of claim 1, wherein the graph representation data comprise vertex features defined as registered native space coordinates.

22. A method for generating brain feature data from medical images, the method comprising:
    (a) accessing medical image data with a computer system, wherein the medical image data comprise medical images that depict a brain of a subject;
    (b) accessing a neural network with the computer system, wherein the neural network is trained to take input as brain surface data and generate output as brain feature data;
    (c) generating graph representation data of the medical image data using the computer system, wherein the graph representation data represent a mapping of the medical image data onto a graph of connected nodes;
    (e) inputting the graph representation data to the neural network, generating output as brain feature data that indicate at least one brain feature of the subject's brain; and
    (f) outputting the brain feature data to a user.

* * * * *